US008674172B2

(12) United States Patent
Chauchereau et al.

(10) Patent No.: US 8,674,172 B2
(45) Date of Patent: Mar. 18, 2014

(54) PROSTATE CANCER CELL LINES AND THEIR USE IN SCREENING METHOD

(75) Inventors: Anne Chauchereau, Fontenay-Aux-Roses (FR); Karim Fizazi, Saint Mande (FR); Catherine Gaudin, Savigny sur Orge (FR); Nader Al Nakouzi, Amchit (LB); Jean Benard, L'Hay les Roses (FR)

(73) Assignee: Institut Gustave Roussy, Villejuif Cedex (FR)

( * ) Notice: Subject to any disclaimer, the term of this patent is extended or adjusted under 35 U.S.C. 154(b) by 0 days.

(21) Appl. No.: 13/264,479

(22) PCT Filed: Apr. 12, 2010

(86) PCT No.: PCT/EP2010/054739

§ 371 (c)(1),
(2), (4) Date: Oct. 14, 2011

(87) PCT Pub. No.: WO2010/119001

PCT Pub. Date: Oct. 21, 2010

(65) Prior Publication Data

US 2012/0036587 A1 Feb. 9, 2012

(30) Foreign Application Priority Data

Apr. 14, 2009 (EP) .................................... 09305315
Feb. 24, 2010 (EP) .................................... 10154473

(51) Int. Cl.

| | |
|---|---|
| ***G01N 33/48*** | (2006.01) |
| ***C12N 5/09*** | (2010.01) |
| ***C12Q 1/18*** | (2006.01) |
| ***C12Q 1/02*** | (2006.01) |
| ***C12Q 1/68*** | (2006.01) |
| ***A01K 67/027*** | (2006.01) |

(52) U.S. Cl.

USPC .................. 800/3; 435/375; 435/32; 435/29; 435/6.1; 800/10

(58) Field of Classification Search

None

See application file for complete search history.

(56) References Cited

FOREIGN PATENT DOCUMENTS

| | | |
|---|---|---|
| WO | WO 99/19479 | 4/1999 |
| WO | WO 00/44879 | 8/2000 |

OTHER PUBLICATIONS

Chauchereau et al. (American Society of Clinical Oncology: 2007 Prostate Cancer Symposium. General Poster Session A; Abstract No. 59).*

Souza et al. (British Journal of Cancer. 1997; 75(11): 1593-1600).*

Andresen, C. et al. "Intra-tibial injection of human prostate cancer cell line CWR22 elicits osteoblastic response in immunodeficient rats" *J. Musculoskel Neuron Interact*, 2003, pp. 148-155, vol. 3, No. 2, XP-002587166.

Havens, A. M. et al. "An In Vivo Mouse Model for Human Prostate Cancer Metastasis" *Neoplasia*, Apr. 2008, pp. 371-379, vol. 10, No. 4, XP-002587167.

Koochekpour, S. et al. "Establishment and Characterization of a Primary Androgen-Responsive African-American Prostrate Cancer Cell Line, E006AA" *The Prostate*, 2004, pp. 141-152, vol. 60, XP-002562706.

Sallman, D. A. et al. "Clusterin mediates TRAIL resistance in prostate tumor cells" *Mol. Cancer Ther.*, Nov. 2007, pp. 2938-2947, vol. 6, No. 11, XP-002562707.

Selvan, S. R. et al. "Establishment and Characterization of a Human Primary Prostate Carcinoma Cell Line, HH870" *The Prostate*, 2005, pp. 91-103, vol. 63, XP-002562705.

Sowery, R. D. et al. "Clusterin knockdown using the antisense oligonucleotide OGX-011 re-sensitizes docetaxel-refractory prostate cancer Pc-3 cells to chemotherapy" *BJU International*, 2008, pp. 389-397, vol. 102, XP-002562708.

Virk, M. S. et al. "Influence of simultaneous targeting of the bone morphogentic protein pathway and RANK/RANKL axis in osteolytic prostate cancer lesion in bone" *Bone*, 2009, pp. 160-167, vol. 44, XP-002587168.

Written Opinion in International Application No. PCT/EP2010/054739, Jun. 15, 2010, pp. 1-6.

* cited by examiner

*Primary Examiner* — Scott Long

(74) *Attorney, Agent, or Firm* — Saliwanchik, Lloyd & Eisenschenk

(57) ABSTRACT

The present invention relates to a prostate cancer cell line CNCM deposit number I-4126, the use thereof for preparing resistant prostate cancer cell lines, the resistant prostate cancer cell lines, and the use of these prostate cancer cell lines for screening compounds of interest.

12 Claims, 11 Drawing Sheets

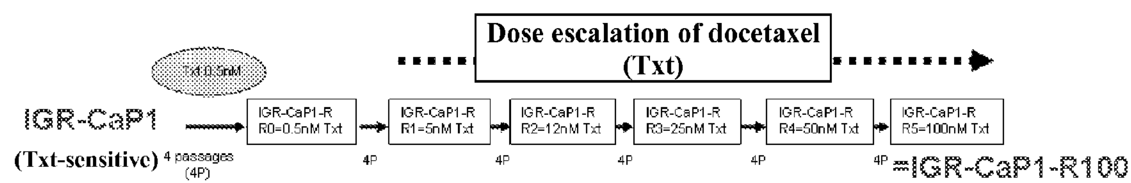
FIGURE 3
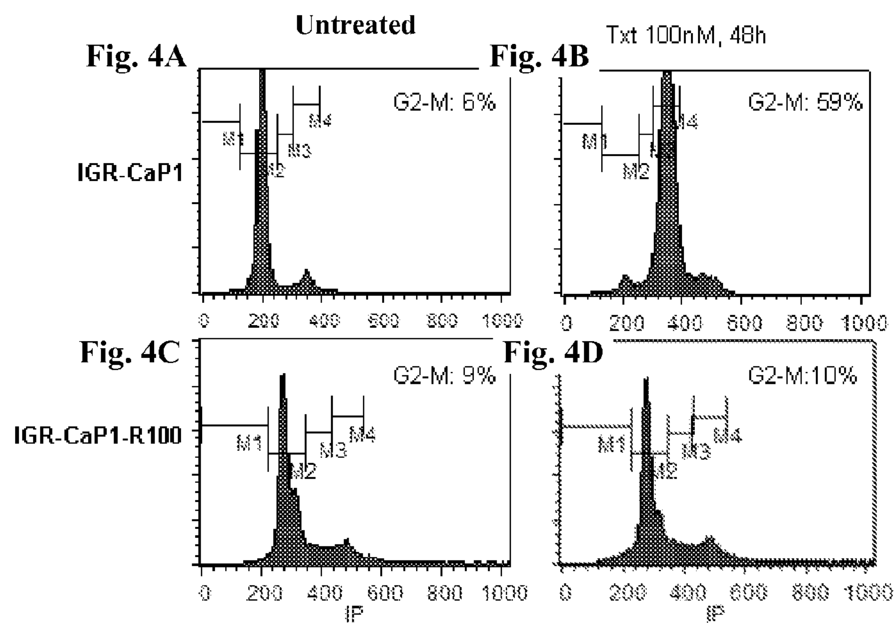

| | | IGR-CaP1 | IGR-CaP1-R100 |
|---|---|---|---|
| Locus ID | D8S1179 | 13-14-15-16-17 | 13-14-16-17 |
| | D21S11 | 26-30.2 | 26-30.2 |
| | D7S820 | 9.1-10.1-11.2 | 9.1-10.1-11.2 |
| | CSF1PO | 11-14-16 | 11-12-14-15-16 |
| | D3S1358 | 14-15 | 14-15 |
| | TH01 | 7-8-9.3 | 6-7-8-9.3 |
| | D13S317 | 8-10 | 8-10 |
| | D16S539 | 11-12-13 | 10-11-12-13 |
| | D2S1338 | 17-24-25 | 17-24-25 |
| | D19S433 | 13-14 | 13-14 |
| | vWA | 16-20-21 | 16-20-21 |
| | TPOX | 8-10-11 | 8-10-11 |
| | D18S51 | 14-15-16 | 15-16 |
| | amelogenin | X | X |
| | D5S818 | 12-13 | 12-13 |
| | FGA | 20-21-25-26 | 19-20-21-25 |

PROSTATE CANCER CELL LINES AND THEIR USE IN SCREENING METHOD

CROSS-REFERENCE TO RELATED APPLICATION

This application is the U.S. national stage application of International Patent Application No. PCT/EP2010/054739, filed Apr. 12, 2010.

FIELD OF THE INVENTION

The present invention relates to the oncology and the identification of new drugs for the treatment of prostate cancer.

BACKGROUND OF THE INVENTION

Prostate cancer is the leading cause of cancer-related deaths in North America and Europe. Localized prostate tumours are commonly diagnosed and conventionally treated by radical prostatectomy. After an initially effective hormone therapy, the advanced disease led to the development of hormone-refractory, drug-resistant malignancy. To date, there is still no cure available for patients with advanced disease.

Cell cultures established directly from patient tumors are powerful research resource for studying cancer cell biology and for the development of new strategies against cancer. Some cellular or xenografted models have been established from different tissue origins but most of these models have been obtained from prostate tumor metastases or have been artificially established.

Over the years a number of new cell lines and clonal derivatives of these original lines have been developed by investigators using a variety of methods. Although there is a real need of identifying cells at the origin of prostate cancer, there are still few culture models to study the early step of the oncogenesis of prostate cancer. Therefore it is still a challenge to obtain new cancer models that may better reflect the mechanisms of local tumor progression and to identify cells at the origin of prostate cancer, potentially including cancer stem cells.

Human prostate cells are known to be one of the most difficult cell types to develop into continuously growing culture and considerable research efforts have been directed toward the establishment of new prostate cancer models from the primary tumours.

In view of the difficulties to obtain human prostate cancer cell lines, several teams developed immortalization approaches of prostate tissues, often benign ones. Thereby, several epithelial cell lines were obtained by immortalization with SV40 large T-antigen. However, the major impact of SV40 large T-antigen, a potent oncogene, in their preparation makes these cell lines a very artificial model of prostate cancer. Alternatively, human telomerase catalytic subunit (hTERT) has been successfully used to immortalize human prostate epithelial (HPE) cells from normal prostate or primary tumors, named HPET cells. Several groups had chosen this strategy and established immortalized cultures which are to date the most representative of the authentic prostate cancer cells (Yasunaga et al., 2001; Gu et al., 2004; Litvinov et al., 2006; Daly-Burns et al. 2007; Gu et al., 2007; Miki et al., 2007).

Yet, only two continuously cultured human primary epithelial prostate cancer cell lines have been obtained, the E006AA cell lines (Koochekpour et al., 2004) and the HH870 (Selvan et al., 2005), with very few available published results. Three other cell lines established from a primary tumor are only maintained in xenograft (van Bokhoven et al., 2003). A third human prostate cancer model was recently established in vitro from a trans-rectal prostate needle biopsy specimen but it was unable to grow in nude mice (Attard et al., 2009). Currently, prostate cancer models, directly derived from primary tumors, enabling both in vivo and in vitro approaches and representing the early stages of this cancer are still lacking.

Since 2004, docetaxel (Taxotere®) is become the reference treatment of hormone-resistant metastatic prostate cancer. However, despite the survival benefit of this drug, a high number of patients treated with docetaxel develop a chemotherapy resistance. This is why cellular models of prostate cancer resistant to docetaxel are so interesting and useful.

In order to study the resistance to drugs, several teams obtained prostate cancer models resistant to different drugs. DU145 and PC3 cells resistant to docetaxel or paclitaxel (Makarovskiy et al., 2002; Patterson et al., 2006; Takeda et al, 2007) and LNCaP cells resistant to cisplatin (Nomura et al., 2005) were obtained and are used by several groups in different studies (Kucukzeybek et al., 2008; Erten et al., 2009; Lo Nigro et al., 2008; Sowery et al., 2008; Sallman et al., 2007).

The use of cellular models is useful to eliminate the cytotoxic compounds in the early and later stages of drug discovery that can help reduce the costs of research and development. In prostate cancer, the investigators are now focused on how to enhance the cytostatic and cytotoxic effects of docetaxel by combining it with novel anticancer agents for the treatment of prostate cancer. The use of docetaxel-resistant and the corresponding parental prostate cancer cell lines is thus an indispensable tool to assess new drug efficacy.

Furthermore, the search for correlations between gene expression profiles and chemosensitivity has been initiated on in vitro models in large screening projects. The best example is the set of 60 human tumor cell lines of the US National Cancer Institute (NCI) designed for the screening of 3,000 compounds per year for potential anticancer activity (Shoemaker, 2006). This strategy may certainly allow for progress in the identification of individual patients who may benefit from a specific chemotherapy.

Moreover the availability of drug-resistant cellular models with tumorigenic properties offers the possibility to establish animal models useful for both biomarkers identification and screening of potential therapeutic agents.

Consequently, a prostate cancer cell line, either sensitive or resistant to a cytotoxic drug, is of great interest for pharmaceutical companies.

SUMMARY OF THE INVENTION

The inventors established a new prostate cancer cell line, called IGR-CaP1, from a localized prostate tumor and a derived cell line called IGR-CaP1-R100 resistant to docetaxel.

Accordingly, the present invention provides a prostate cancer cell line designated IGR-CaP1 as described in CNCM deposit number 1-4126 on Feb. 10, 2009, or a progeny thereof.

From this prostate cancer cell line, some resistant cell lines can be prepared. Therefore, the present invention concerns a method for preparing a prostate cancer cell line resistant to a dose of a cytotoxic drug comprising submitting the prostate cancer cell line IGR-CaP1 to increasing doses of the cytotoxic drug and selecting the resulting prostate cancer cells resistant to the dose of the cytotoxic drug. The present invention also concerns the use of the prostate cancer cell line IGR-CaP1 for preparing a prostate cancer cell line resistant to a dose of a cytotoxic drug and any prostate cancer cell line resistant to a dose of a cytotoxic drug prepared from the prostate cancer cell line IGR-CaP1. In a particular embodiment, the present invention concerns the prostate cancer cell line resistant to 100 nM of docetaxel and designated IGR-CaP1-R100 as described in CNCM deposit number 1-4127 on Feb. 10, 2009, or a progeny thereof.

The present invention further concerns a kit for screening potential therapeutic agents comprising a prostate cancer cell line according to the present invention.

In addition, the present invention concerns an animal model comprising a prostate cancer cell according to the present invention. In a particular embodiment, the animal model comprises a prostate cancer cell resistant to a cytotoxic drug according to the present invention.

The present invention concerns the use of a prostate cancer cell line or an animal model according to the present invention for screening potential therapeutic agents.

In particular, the present invention concerns a method for determining whether a candidate agent inhibits proliferation of a prostate cancer cell line according to the present invention comprising: a) contacting the prostate cancer cell line of the present invention with the candidate agent; and b) measuring the proliferation of the prostate cancer cell line so contacted, a reduction in proliferation indicating that the candidate agent inhibits proliferation of the prostate cancer cell line. Alternatively, it concerns a method for determining whether a candidate agent increases the sensitivity to a cytotoxic drug of a prostate cancer cell line according to the present invention resistant to said cytotoxic drug comprising: a) contacting the prostate cancer cell line resistant to said cytotoxic drug of the present invention with the candidate agent in presence of the cytotoxic drug; and b) measuring the proliferation of the cell line so contacted, a reduction in proliferation indicating that the candidate agent increases the sensitivity of the prostate cancer cell line to the cytotoxic drug. Preferably, the proliferation of the cells in step b) is measured using a method selected from a group consisting of DNA cell cycle method, 3H-thymidine incorporation method, cell count method, colorimetric cell proliferation assay or efficiency of colony formation method. The candidate agent can be a chemical molecule, a polypeptide, a nucleic acid molecule, an antibody, a metal, a radiotherapy or a combination thereof.

The present invention also concerns a method for determining whether a candidate agent inhibits proliferation of a prostate cancer cell line according to the present invention which comprises: a) administering the candidate agent to an animal model comprising a prostate cancer cell according to the present invention; and b) measuring the proliferation of the prostate cancer cells in the animal model, a reduction in proliferation indicating that the candidate agent inhibits proliferation of the prostate cancer cells. Alternatively, it concerns a method for determining whether a candidate agent increases the sensitivity to a cytotoxic drug of a prostate cancer cell line according to the present invention resistant to said cytotoxic drug comprising: a) administering the candidate agent to an animal model comprising a prostate cancer cell resistant to the cytotoxic drug according to the present invention in combination with the cytotoxic drug; and b) measuring the proliferation of the prostate cancer cells in the animal model, a reduction in proliferation indicating that the agent increases the sensitivity of the prostate cancer cell line to the cytotoxic drug. Preferably, the animal model presents a tumor formed by the prostate cancer cell line and wherein the proliferation of the prostate cancer cells in the animal model is measured by the determination of the tumor size.

BRIEF DESCRIPTION OF THE DRAWINGS

FIG. 1: Morphology and epithelial features of the IGR-CaP1 cell line.

FIG. 2: High tumorigenic features of IGR-CaP1 cell line.

FIG. 3: Protocol used for preparing IGR-CaP1-R100 cell line resistant at 100 nM of docetaxel. Cells are submitted to increasing doses of docetaxel (Txt), for at least four successive passages for each dose before increasing the dose.

FIG. 4: Cellular cycle comparison of IGR-CaP1 cell line sensitive to docetaxel (A and B) and of IGR-CaP1-R100 cell line resistant to a dose of 100 nM of docetaxel (C and D). If cells are treated by 100 nM of docetaxel for 48 h, sensitive cells are blocked in G2-M phase (B) whereas resistant cells normally cycle (D). Cell cycle measurement was performed by flow cytometry after propidium iodide incorporation.

FIG. 7: Cell growth and kinetics.

FIG. 8: Absence of AR and PSA expression in IGR-CaP1 cells.

Figure 9A:
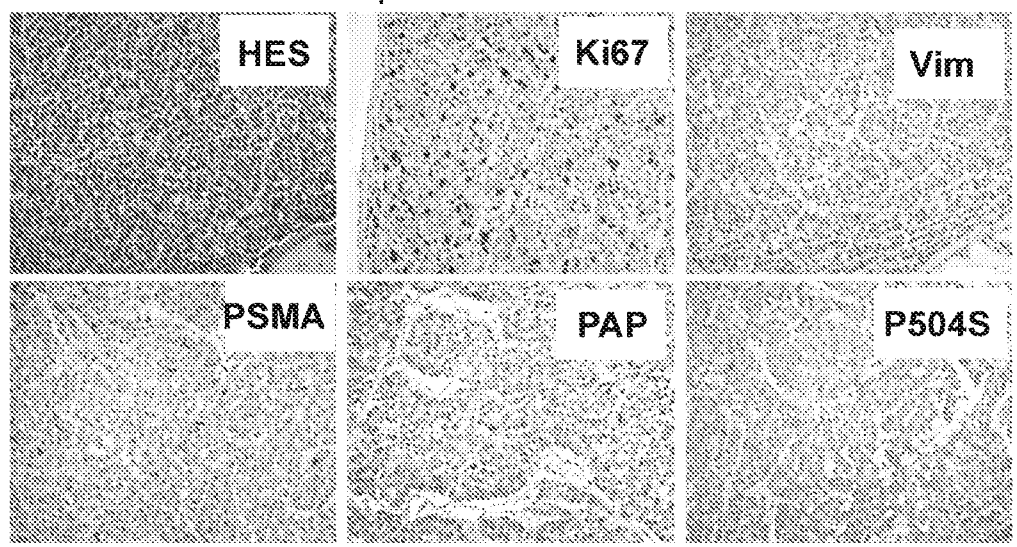
FIG. 9: IGR-CaP1 cells reconstitute adenocarcinoma in mice. IGR-CaP1 cells were injected into male nude mice both intraprostatically (FIG. 9A) and subcutaneously (FIG. 9B).
Figure 9B:
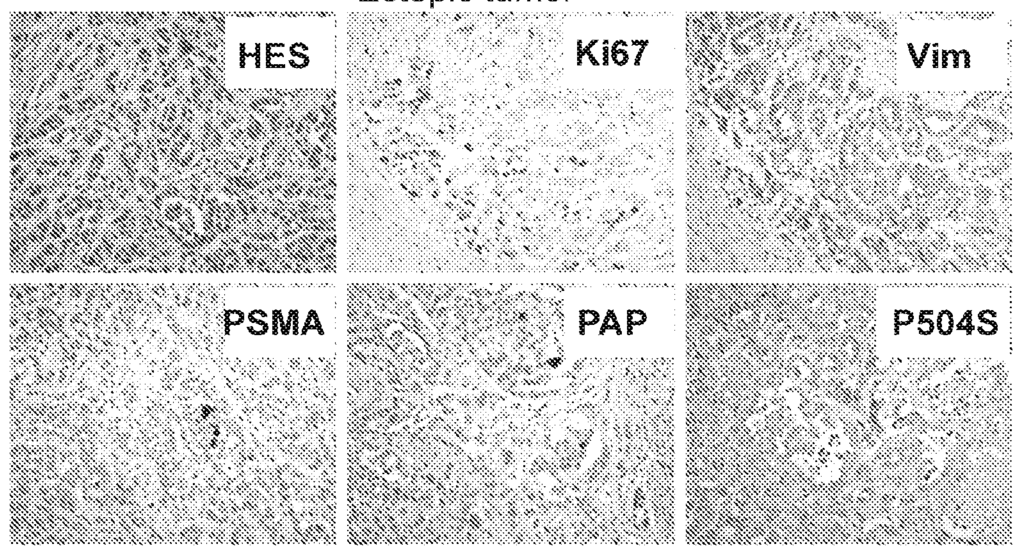
Figure 9C:
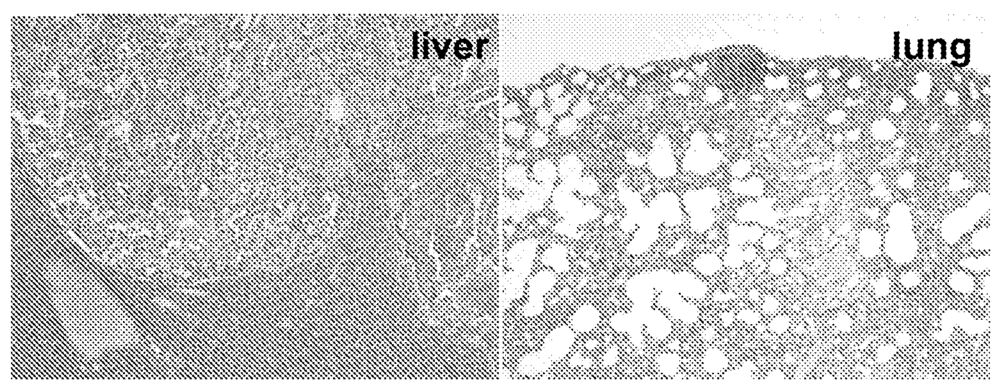

HES-staining section of the tumours (HES) revealed a glandular differentiation with ascini attesting the presence of adenocarcinoma. The proliferation index was shown by the staining of Ki67. The staining corresponding to Vimentin was only shown in ectopic tumors. The prostatic markers corresponding to the prostatic acid phosphatase (PAP) and the prostate secreted membrane antigen (PSMA) attested from the prostate origin of the tumour. A low AMACR (P504S) staining was also observed in both tumour types. HES-staining section of metastases mostly observed in the liver and in the lungs (FIG. 9C).

Figure 10:
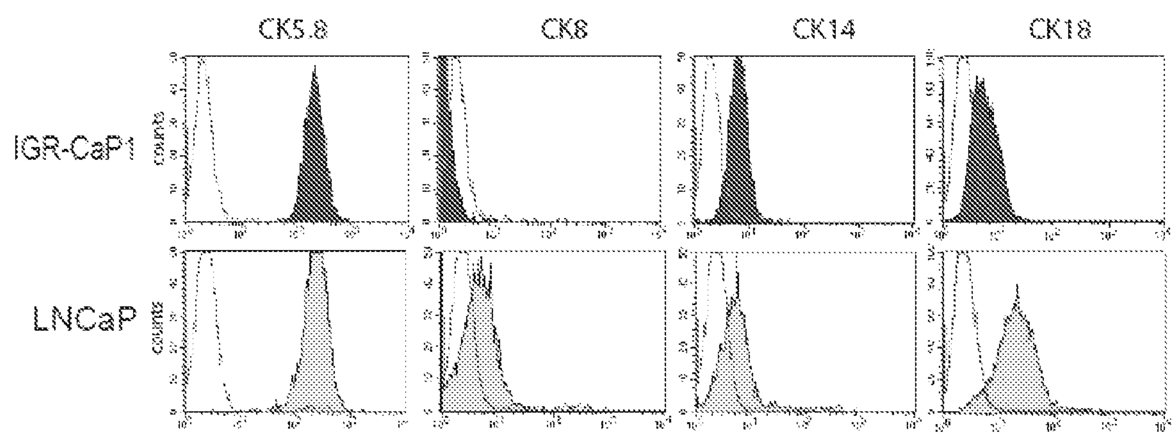

FIG. 10: Basal-type of the cytokeratin profile of the IGR-CaP1 cell line. The expression of cytokeratin markers CK5, CK8, CK14 and CK18 were measured in IGR-CaP1 cells by cytometer analysis in comparison with that of the luminal epithelial prostate LNCaP cell line as control. IGR-CaP1 cells exhibit strong staining for CK5/8 and CK14 but absence of staining for CK8, corresponding to a basal epithelial profile.

Figure 11A:
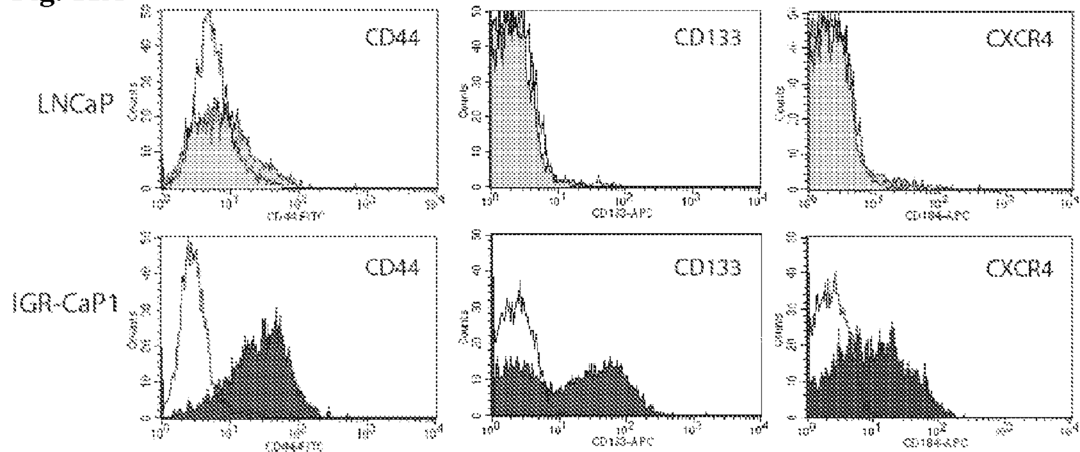
Figure 11B:
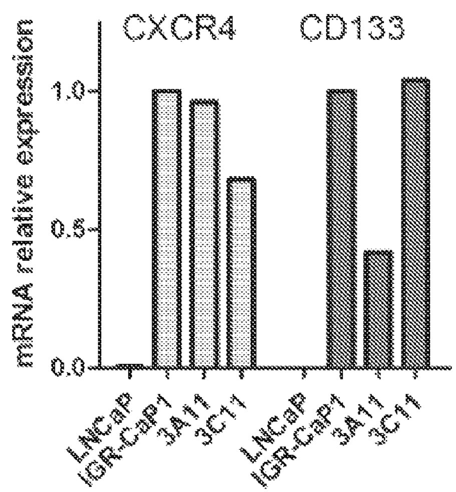
Figure 11C:
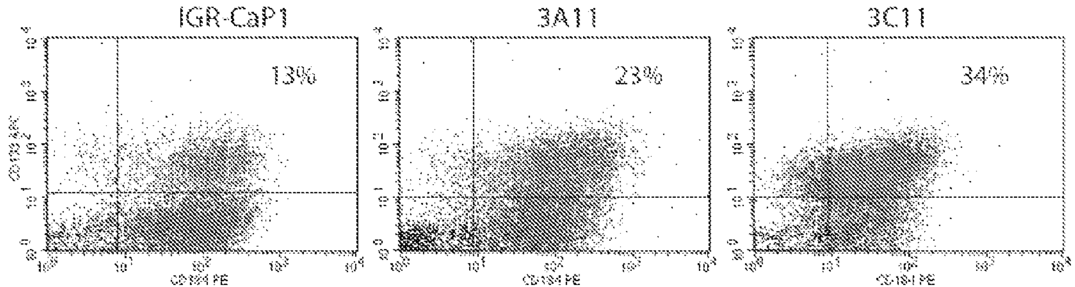

FIG. 11: Cancer stem cell marker expression in the IGR-CaP1 cell line and in two clonally-derived clones. (FIG. 11A) The expression level of the stem cell marker CD44, CD133 and CXCR4 were measured by flow cytometry in comparison to LNCaP cell line. (FIG. 11B) Gene expression of CD 133 and CXCR4 were measured by real-time quantitative RT-PCR in the parental IGR-CaP1 cell line and in the clonally-derived clones 3A11 and 3C11. (FIG. 11C) The combination of the biomarkers expression CD44/CD133/CXCR4 was measured by flow cytometry using CD44-FITC, CD133-APC and CD184-PE, in the parental IGR-CaP1 cell line and in the clonally-derived clones 3A11 and 3C11, showing a high percentage of triple positive in the derived clones 3A11 and 3C11.

Figure 12A:
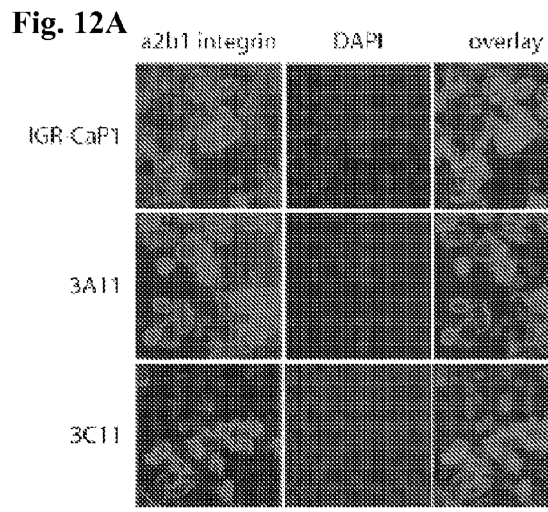
Figure 12B:
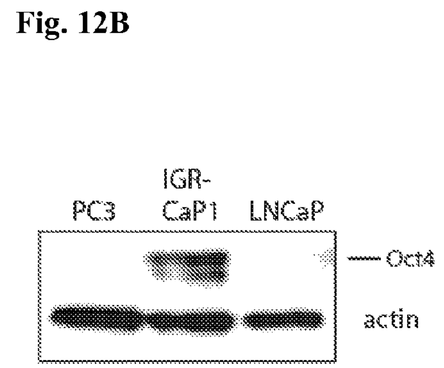
Figure 12C:
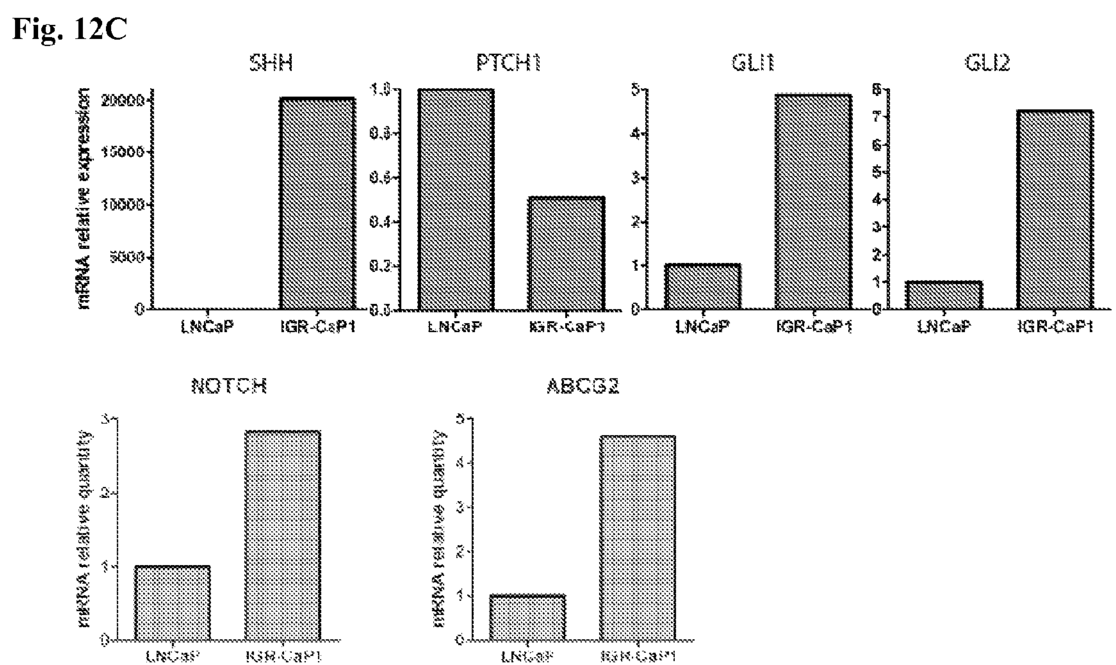

FIG. 12: Stem cell signalling pathways in IGR-CaP1 cells. (FIG. 12A) $\alpha 2\beta 1$ integrin was measured by immunofluorescence in the parental IGR-CaP1 cell line and in the clonally-derived clones 3A11 and 3C11. The nuclei were counter-stained with Dapi. (FIG. 12B) The expression of the transcription factor Oct4 was measured by western blot analysis in the IGR-CaP1 cells in comparison to PC3 and LNCaP cells. (FIG. 12C) Real-time RT-PCR was used to determine the expression level of several markers recently identified as regulator of normal prostate stem/progenitor cells. Compared to LNCaP cells, Sonic Hedgehog (SHH) gene was much more expressed in the IGR-CaP1 cells. NOTCH and ABCG2 gene expression were also more expressed in IGR-CaP1 cells than in LNCaP cells but to a less extend than SHH.

Figure 13:
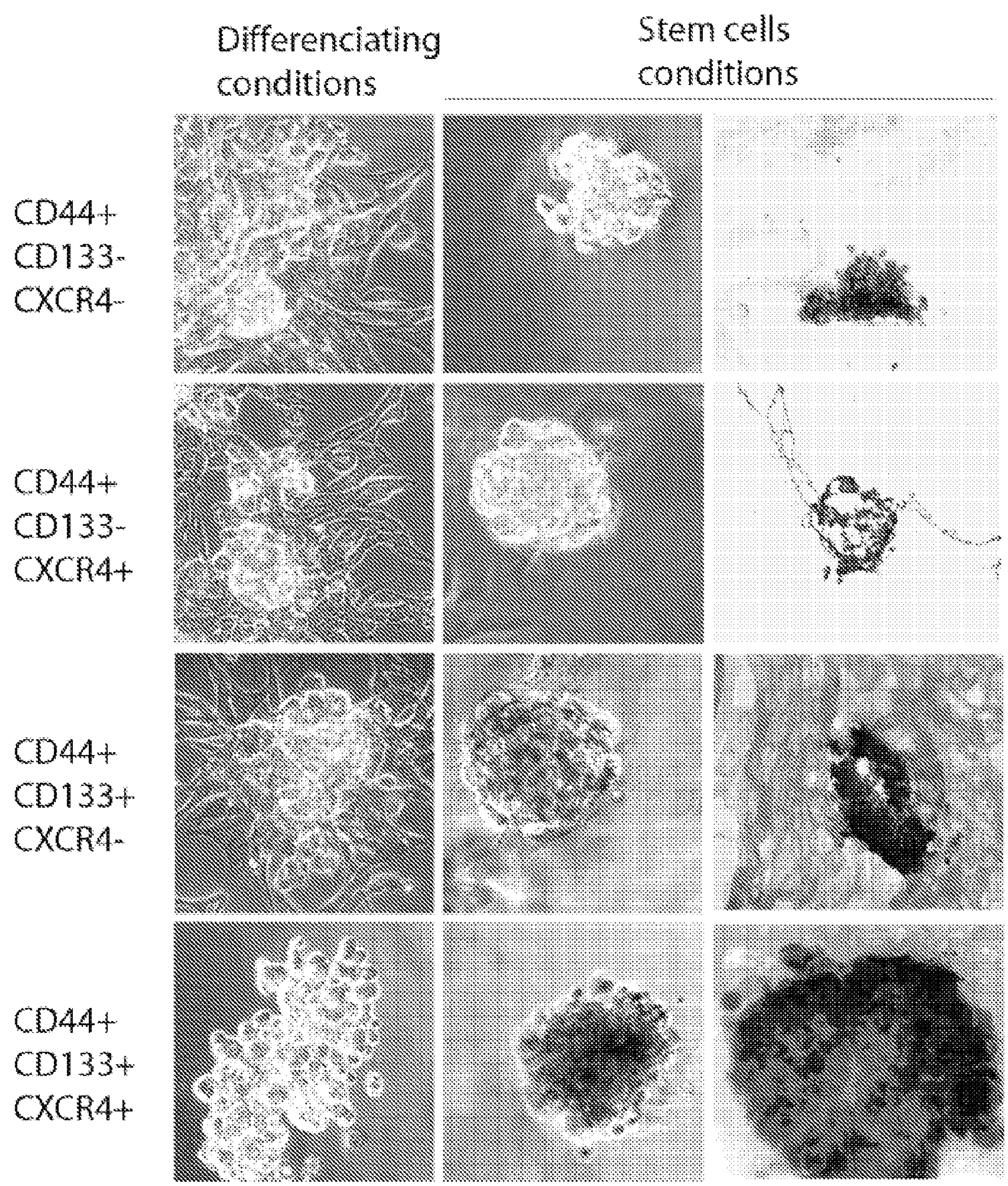

FIG. 13: Phenotypic differentiation of cell-sorted IGR-CaP1 cells after culturing in 3D Matrigel. After cell sorting based on the expression of the stem cell markers CD44, CD133 and CXCR4, cells were cultured under 3D differentiating or stem cell conditions in matrigel over 4 weeks. Photomicrographs showing "spheroids" of sorted cells cultured in stem cell conditions and representative HES-stained sections (40×).

FIG. 14: Bone remodelling after direct injection of cells IGR-CaP1 in the tibia of nude mice. FIGS. 14A and 14B: Representative high-resolution scanner (XCT) on nude mice tibias at 10 weeks following intratibial injection of IGR-CaP1 cells, coronal (FIG. 14A) and surface rendering (FIG. 14B). FIGS. 14C and 14D: bone scintigraphy (SPECT/X CT) with mT99-MDP showing extensive bone remodelling, as indicated by the arrow (FIG. 14C) and quantified by determination of the % of the radioactivity binding in each tibia (FIG. 14D). Results are the mean±SD of results obtained on 6 injected animals. FIGS. 14E and 14F: HES-staining of IGR-CaP1 intratibial tumor. Photographs were taken at magnification ×25 (FIG. 14E) and 200× (FIG. 14F). Stars point to IGR-CaP1 tumor cells, arrows point to new bone formation.

DETAILED DESCRIPTION OF THE INVENTION

The inventors established and characterized a new prostate cancer cell line, called IGR-CaP1. This cell line has the advantage to be a cancer prostate cell line obtained from a primary localized tumor (contrary to almost all other prostate cancer cell lines obtained from metastasis). The molecular characterization of the cell line suggests that these cells correspond to prostate epithelial basal cells. These cells were spontaneously immortalized; exhibit a tetraploid karyotype and a high telomerase activity. IGR-CaP1 cells do not express androgen receptor protein (AR) or secretory prostate-specific antigen (PSA). Contrarily to prostate epithelial luminal cells which express AR and secrete PSA such as E006AA cells, basal prostate epithelial cells are particularly important as the basal cell compartment is thought to contain the epithelial stem or progenitor cells. Cancer stem cells have the property of self-renewal and the capacity of differentiation reflecting the tumor from which they were derived. So, prostate cancer stem cells have the capacity to differentiate into AR-expressing luminal cells. According to this new concept, it is assumed today that cancer stem cells could be those who may be responsible for the development of drug resistance and disease progression and thus constitute the most appropriate cells to kill. In mice, the IGR-CaP1 cell line recapitulates the characteristics of an undifferentiated prostate tumor observed in patients with a high Gleason score. In particular, it is tumorigenic in nude mice where it forms tumors reconstituting adenocarcinoma expressing prostate markers PSMA and PAP and capable of metastasizing. Strikingly, data obtained after intra-tibia injections of the IGR-CaP1 cell in nude mice showed both osteoblastic and osteolysis lesions corresponding to bone remodelling, as regularly observed in patient bone metastases. The IGR-CaP1 cell line is then the first prostate cancer cell line established from a primary tumor which is able to induce osteoblastic and osteolysis lesions. These cells express markers described as cancer stem cells in some solid tumors (CD44, CD133) and in prostate cancer cellular models (CD44, CD133, $\alpha 2\beta 1$ integrin, CXCR4). By subcloning the IGR-CaP1 cell line, the inventors obtained cellular derived-clones exhibiting the original features of prostate tissue and conserving cancer stem cell properties. As it is believed that cancer stem cells may be a major cause of drug resistance and contribute to disease recurrence in prostate cancer patients, these new models are useful for developing new therapeutic approaches targeting prostate cancer stem cells.

Therefore, the present invention concerns the new prostate cancer cell line, called IGR-CaP1, which has been deposited at the CNCM (Collection Nationale de Culture de Microorganismes at the Pasteur Institute, 25 rue du Dr. Roux, F-75724 Paris Cedex 15, France) on Feb. 10, 2009 under number 1-4126 and any progeny thereof.

As used herein, the expressions "cell," "cell line," and "cell culture" are used interchangeably and all such designations include progeny. In particular, by progeny is also intended cell clones obtained by limit dilution of the cell lines of the invention. Because certain modifications may occur in succeeding generations due to either mutation or environmental influences, or clonal selection, such progeny may not be identical to the parent cell, but are still included within the scope of the term as used herein. However, the STR profile can be used to determine if a cell is a progeny of the IGR-CaP1 cell line. In a particular embodiment, the IGR-CaP1 cell line and its progeny should have the same alleles for D7S820, D13S317, TPDX, and amelogenin loci or at least 10 identical loci among the 16-locus STR multiplex comprising D8S1179, D21S11, D7S820, CSF1P0, D3S1358, TH01, D13S317, D16S539, D2S1338, D19S433, vWA, TPDX, D18S51, amelogenine, D5S818 and FGA loci.

The present invention also contemplates a method for isolating a clonal cell by a limit dilution of a cell line according to the present invention.

The present invention also concerns any cell derived from the IGR-CaP1 cell line, for instance by mutagenesis or by genetic transformation. In a particularly preferred embodiment, the present invention concerns a method for preparing a prostate cancer cell line resistant to a dose of a cytotoxic drug comprising submitting the prostate cancer cell line IGR-CaP1 to increasing doses of the cytotoxic drug and selecting the resulting prostate cancer cell line resistant to the dose of the cytotoxic drug. The present invention also concerns the use of the prostate cancer cell line IGR-CaP1 for preparing a prostate cancer cell line resistant to a dose of a cytotoxic drug. It further concerns a prostate cancer cell line resistant to a dose of a cytotoxic drug prepared from the prostate cancer cell line IGR-CaP1. The term "IGR-CaP1-R" refers herein to a cell line prepared from the prostate cancer cell line IGR-CaP1 and being resistant to a cytotoxic drug.

By "cytotoxic drug" is intended to refer herein to any molecule having a toxic effect on cells. In particular, it refers to any molecule leading to cell death (e.g., by apoptosis or any other mechanism) or inhibiting or suppressing cellular growth and multiplication. Such drugs are commonly used in chemotherapy to inhibit the proliferation of cancerous cells. In a preferred embodiment, the cytotoxic drug is a drug used or useful for the treatment of prostate cancer. For instance, the cytotoxic drug can be selected from the group consisting of docetaxel, paclitaxel and others taxanes, mitoxantrone, platin salts, doxorubicin, vinblastine, estramustine, and etoposide.

The methods for preparing a cell line resistant to a cytotoxic drug or compound are well-known by the artisan skilled in the art. For instance, in order to obtain a resistant cell line from the IGR-CaP1 cell line, a dose escalation can be carried out. In particular, a protocol is disclosed in Materials and Methods Section of Patterson et al (2006), the disclosure of which being incorporated herein by reference. The cells can be contacted with a first dose of the cytotoxic drug. After the clones sensitive to the first dose are no longer present, the surviving cells repopulate the flask and continue to divide through about 4 passages. Then, they are incubated with a higher second dose of the cytotoxic drug. The same methodology is followed with each increase in the concentration of the cytotoxic drug until to reach the dose of the cytotoxic drug at which the cells have to be resistant.

In a particular embodiment, the cytotoxic drug is docetaxel. The inventors prepared, from the IGR-CaP1-R cell line, resistant cell lines to the following docetaxel doses: 0.5 nM, 5 nM, 12 nM, 25 nM, 50 nM, 100 nM, 200 nM and 12 μM.

In a particular embodiment, the present invention concerns the prostate cancer cell line resistant to 100 nM of docetaxel and designated IGR-CaP1-R100 as described in CNCM deposit number 1-4127 on Feb. 10, 2009, or a progeny thereof. This cell line is also resistant to cisplatin.

The IGR-CaP1 cell line and the IGR-CaP1-R cell lines resistant to a cytotoxic drug can be useful for determining or identifying biomarkers for resistance to the cytotoxic drug. Biomarkers identification could be performed by expression profile analysis of sensitive cells and/or of different cells resistant to the same drug and/or cells resistant to the different drugs. It can also be carried out by comparative microarray, RT-PCR, Western Blot, Immunohistochemistry and the like.

In a further embodiment, the IGR-CaP1 cell line and the IGR-CaP1-R cell lines are transformed with an expression vector comprising a gene encoding a marker molecule. Said modified cell lines may be useful to follow the growth of prostatic tumors, in particular of intraprostatic tumors. In a preferred embodiment, the expression vector is a retroviral vector. This vector may be easily chosen by the skilled person from vectors allowing the expression a transgene in mammalian cells. The marker may be selected from well-known markers such as luciferase, Green Fluorescent protein (GFP) and derivatives such as EGFP, blue fluorescent proteins (EBFP, EBFP2, Azurite, mKalama1), cyan fluorescent proteins (ECFP, Cerulean, CyPet) and yellow fluorescent proteins (YFP, Citrine, Venus, YPet), DsRed and derivatives thereof, Keima and derivatives thereof, glucuronidase (GUS), β-Glucosidase, alkaline phosphatase, horseradish peroxidase and beta-galactosidase (LacZ).

The prostate cancer cell lines of the invention are also useful for screening potential therapeutic agents. Therefore, the present invention concerns a kit for screening potential therapeutic agents comprising a prostate cancer cell line of the invention. The kit can further comprise a culture medium appropriate for the prostate cancer cell line. In a particular embodiment, the kit can comprise the IGR-CaP1 cell line and an IGR-CaP1-R cell line resistant to a cytotoxic drug, preferably docetaxel. The present invention also concerns the use of a prostate cancer cell line of the invention or a combination thereof for screening potential therapeutic agents.

The potential therapeutic agents can be a molecule having a cytotoxic or cytostatic effect of the cells. Alternatively, the potential therapeutic agents can be a molecule increasing the efficacy of a drug, increasing or restoring the sensitivity of cells to a drug to which they are resistant, a molecule preventing, reducing, or delaying the appearance in cells of a resistance to a drug. The candidate agent is a chemical molecule, a polypeptide, a nucleic acid molecule, an antibody, or a metal. For instance, a nucleic acid molecule can be a siRNA, an antisense, a ribozyme and the like. The therapeutic agent can also be radiotherapy alone or in combination with chemotherapy.

In a particular embodiment, the present invention concerns a method for determining whether a candidate agent inhibits proliferation of a prostate cancer cell line according to the present invention comprising: a) contacting the prostate cancer cell line of the present invention with the candidate agent; and b) measuring the proliferation of the cell line so contacted, a reduction in proliferation indicating that the candidate agent inhibits proliferation of the cell line. The prostate cancer cell line used in this method can be an IGR-CaP1 cell line or an IGR-CaP1-R cell line resistant to a cytotoxic drug. In the latter case, the method can allow the identification of alternative treatments when a prostate cancer is already resistant to a cytotoxic drug. Of course, a negative control can be carried out in absence of the candidate agent and/or a positive control can be carried out in absence of a cytotoxic drug known to be efficient in the prostate cancer cell line.

In another particular embodiment, the present invention concerns a method for determining whether a candidate agent increases the sensitivity to a cytotoxic drug of a prostate cancer cell line according to the present invention resistant to said cytotoxic drug comprising: a) contacting the prostate cancer cell line resistant to said cytotoxic drug of the present invention with the candidate agent in presence of the cytotoxic drug; and b) measuring the proliferation of the prostate cancer cell line so contacted, a reduction in proliferation indicating that the candidate agent increases the sensitivity of the prostate cancer cell line to the cytotoxic drug. Of course, a control can be carried out in absence of the candidate agent. In a first embodiment, the cell line is contacted simultaneously with both the candidate agent and the cytotoxic drug. In a second embodiment, the cell line is contacted with the cytotoxic drug prior to be contacted with the candidate agent. In a third embodiment, the cell line is contacted with the candidate agent prior to be contacted with the cytotoxic drug. In this method, the cytotoxic capacity of the candidate agent can be assessed in order to be sure that the reduction in proliferation is due to an increase of sensitivity to the cytotoxic drug.

In an additional particular embodiment, the present invention concerns a method for determining whether a candidate agent is able to prevent, reduce, or delay the appearance of resistance to a cytotoxic drug in a prostate cancer cell line of the present invention comprising: a) contacting the prostate cancer cell line of the present invention, sensitive to the cytotoxic drug, with the cytotoxic drug in presence and in absence of the candidate agent; b) measuring the appearance of cells resistant to the cytotoxic drug, a reduction in appearance of cells resistant to the cytotoxic drug indicating that the candidate agent prevents, reduces, or delays the appearance of resistance to a cytotoxic drug in a prostate cancer cell line. In a first embodiment, the cell line is contacted simultaneously with both the candidate agent and the cytotoxic drug. In a second embodiment, the cell line is contacted with the candidate agent prior to be contacted with the cytotoxic drug. The appearance of cells resistant to the cytotoxic drug can be measured by any method known by the artisan skilled in the art. For instance, the resistance appearance can be assessed by counting cells after submitting to the cytotoxic drug. Alternatively, the resistance appearance can be assessed through the cell proliferation.

The proliferation of the cells can be measured using a method selected from a group consisting of DNA cell cycle method, 3H-thymidine incorporation method, cell count method, colorimetric cell proliferation assay, or efficiency of colony formation method. Several colorimetric cell proliferation assays are currently used and commercially available, such as WST1 cell proliferation assay (Cat No 1 644 807 from Roche), MTT cell proliferation assay (BioPionneer) assay, XTT cell proliferation assay (BioPionneer) assay, or calcein cell proliferation assay (Cat. No. QIA128 from Calbiochem).

As the cell lines of the invention, i.e. the IGR-CaP1 and IGR-CaP1-R cell lines, are tumorigenic in nude mice, they can be used to prepare an animal model for cancer, in particular for prostate cancer. Indeed, when the cell lines of the invention are injected into the animal, they reconstitute a tumor, in particular reproducing an adenocarcinoma. In a preferred embodiment, the animal model is a non-human animal. In particular, the animal model includes, without to be limited thereto, mice, rats and rabbits. Indeed, such animal models are necessary to test the efficacy of new potential anti-tumoral drugs for human beings. In particular, the animal models are immuno-deficient. Accordingly, the present invention concerns an animal model comprising a prostate cancer cell according to the present invention. Alternatively, the present invention concerns an animal model comprising a tumor formed by a prostate cancer cell according to the present invention. In one embodiment, the prostate cancer cell is IGR-CaP1 or a progeny thereof. In another embodiment, the prostate cancer cell is an IGR-CaP1-R cell line, in particular, an IGR-CaP1-R cell line resistant to docetaxel, and more particularly IGR-CaP1-R100 cell line.

In healthy subjects, bone homeostasis is maintained by a balance between bone resorption by osteoclasts and bone formation by osteoblasts. However, in bone metastasis, osteoclast and osteoblast activities are increased. If osteoclast activity is predominant, osteolytic lesions are formed. If osteoblast activity is predominant, osteoblastic (or osteocondensing) lesions are formed. The inventors have demonstrated, as illustrated in the experimental section below, that injection of cell lines of the invention in bones, such as tibia, leads to an intensive bone remodelling with osteolytic and osteoblastic lesions characterizing prostate bone metastasis. This characteristic is particularly interesting because there is currently no animal model that recapitulates spontaneous clinical prostate cancer bone metastases. Accordingly, the present invention concerns an animal model comprising osteolytic and/or osteoblastic lesions formed by prostate cancer cell according to the present invention. In one embodiment, the prostate cancer cell is IGR-CaP1 or a progeny thereof. In another embodiment, the prostate cancer cell is an IGR-CaP1-R cell line, in particular, an IGR-CaP1-R cell line resistant to docetaxel, and more particularly IGR-CaP1-R100 cell line. The animal model of the present invention may be obtained by injecting cell lines of the invention into a bone such as tibia or femur. The animal model may also be obtained by intracardial injection of cell lines of the invention.

The animal model comprising the prostate cancer cell lines of the invention are also useful for screening potential therapeutic agents. Therefore, the present invention concerns the use of an animal model of the invention or a combination thereof an animal model with sensitive cells and resistant cells for screening potential therapeutic agents. The potential therapeutic agents can be a molecule having a cytotoxic or cytostatic effect of the cells or a molecule increasing the efficacy of a drug, increasing or restoring the sensitivity of cells to a drug to which they are resistant, preventing, reducing, or delaying the appearance in cells of a resistance to a drug. The candidate agent is a chemical molecule, a polypeptide, a nucleic acid molecule, an antibody, a metal, a radiotherapy or a combination thereof.

The present invention concerns a method for determining whether a candidate agent inhibits proliferation of the prostate cancer cell line according to the present invention which comprises: a) administering the candidate agent to the animal model of the present invention; and b) measuring the proliferation of the prostate cancer cells in the animal model, a reduction in proliferation indicating that the candidate agent inhibits proliferation of the prostate cancer cell. Preferably, the animal model comprises a tumor formed by the prostate cancer cell line and the proliferation of the prostate cancer cells in the animal model is measured by the determination of the tumor size. The size of the tumor is measured at the beginning (before the treatment with a candidate agent) and during the treatment with a candidate agent. Alternatively, the size of the tumor can be measured until the recurrence (the effect is not always observed during the treatment but sometimes after). The tumor size can be measured directly or indirectly. In a particular embodiment, the prostate cancer cells are beforehand transformed with a vector allowing the expression of a fluorescent marker such as GFP or a luminescent marker such luciferase. In the latter, the tumor cells emit light after injecting luciferin and this emitted light can be measured in asleep animals, the emitted light being proportional to the tumor size. Several dose of the candidate agent can be used. Of course, the size of the tumor is preferably compared to the one of a non-treated animal.

The present invention further concerns a method for determining whether a candidate agent could be used to treat or prevent prostate cancer bone metastases which comprises: a) administering the candidate agent to the animal model of the present invention comprising osteolytic and/or osteoblastic lesions formed by prostate cancer cell according to the present invention; and b) measuring the proliferation of the prostate cancer cells from said lesions in the animal model, a reduction in proliferation indicating that the candidate agent could be used to treat or prevent prostate cancer bone metastases. Preferably, the animal model comprises osteolytic and/or osteoblastic lesions formed by the prostate cancer cell line of the invention and the proliferation of the prostate cancer cells in the animal model is measured by the determination of bone lesion extent and/or bone activity induced by bone remodelling.

As used herein, the term "bone activity" refers to the sum of the bone tissue formation by osteoblasts, i.e. osteogenesis, and the bone resorption by osteoclasts. This activity may be measured by any method known by the skilled person. As example, the bone activity can be measured by bone scintigraphy with Tc99m-Methylene-di-Phosphonate (Tc99m-MDP). Tc99m-MDP bone fixation is determined by osteoblastic activity. Accordingly, osteoblastic lesions induced an increase of Tc99m-MDP fixation whereas osteolytic lesions induced a decrease or an absence of Tc99m-MDP fixation.

Bone lesion extent and/or bone activity is evaluated at the beginning (before the treatment with a candidate agent) and during the treatment with a candidate agent. Alternatively, bone lesion extent and/or bone activity can be measured until the recurrence (the effect is not always observed during the treatment but sometimes after). The bone lesion extent and/or bone activity can be measured directly or indirectly. In a particular embodiment, the bone lesion extent is measured by autoradiography or by high-resolution scanner. In another particular embodiment, the bone activity is measured by bone scintigraphy. Bone lesion extent and/or bone activity is then compared to the one of a non-treated animal. The present invention also concerns a method for determining whether a candidate agent could be used to prevent prostate cancer bone metastases which comprises: a) injecting prostate cancer cells of the invention to an animal, (b) administering the candidate agent to said animal before appearance of osteolytic and/or osteoblastic lesions, and c) measuring the proliferation of the injected prostate cancer cells in said animal and/or the appearance of osteolytic and/or osteoblastic lesions, a reduction in proliferation and/or appearance of osteolytic and/or osteoblastic lesions indicating that the candidate agent could be used to prevent prostate cancer bone metastases. Prostate cancer cells of the invention may be administered in a bone or in the heart of the animal, preferably in a bone of said animal. In an embodiment, the proliferation of the prostate cancer cells in the animal is measured by the determination of bone lesion extent and/or bone activity induced by bone remodelling, as described above. Bone lesion extent and/or bone activity and/or bone lesion number is then compared to the one of an animal in which prostate cancer cells of the invention have been injected but no candidate agent has been administered.

The present invention also concerns a method for determining whether a candidate agent increases the sensitivity to a cytotoxic drug of a prostate cancer cell line according to the present invention resistant to said cytotoxic drug comprising: a) administering the candidate agent to an animal model comprising a prostate cancer cell resistant to the cytotoxic drug according to the present invention in combination with the cytotoxic drug; and b) measuring the proliferation of the prostate cancer cells in the animal model, a reduction in proliferation indicating that the agent increases the sensitivity of the prostate cancer cell line to the cytotoxic drug. Preferably, the animal model comprises a tumor formed by the prostate cancer cell line and the proliferation of the prostate cancer cells in the animal model is measured by the determination of the tumor size. The size of the tumor is measured at the beginning (before the treatment with a candidate agent) and during the treatment with a candidate agent. Several dose of the candidate agent can be used in combination with the cytotoxic drug. Of course, the size of the tumor is preferably compared to the one of an animal non-treated with the candidate agent. In a first embodiment, both the candidate agent and the cytotoxic drug are simultaneously administrating to the animal model. In a second embodiment, the cytotoxic drug is administrating to the animal model prior to the candidate agent. In a third embodiment, the candidate agent is administrating to the animal model prior to the cytotoxic drug.

Further aspects and advantages of this invention will be disclosed in the following examples, which should be regarded as illustrative and not limiting the scope of this invention.

EXAMPLES

Results

IGR-CaP1 Cell Line Constitutes a Prostate Cancer Epithelial Cell Line

Figure 1A:
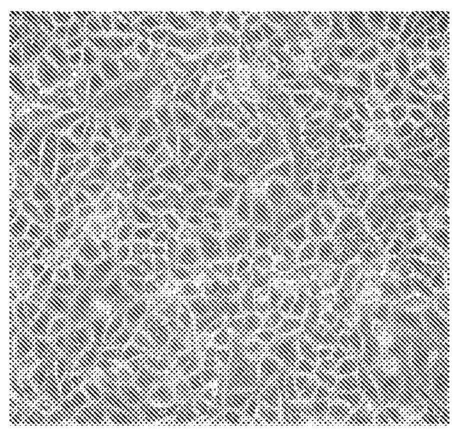
(FIG. 1A) Photomicrograph of human primary prostate cancer cell line IGR-CaP1 (passage 29) grown on the extracellular matrix PX004 that shows typical epithelial morphology.
Figure 1B:
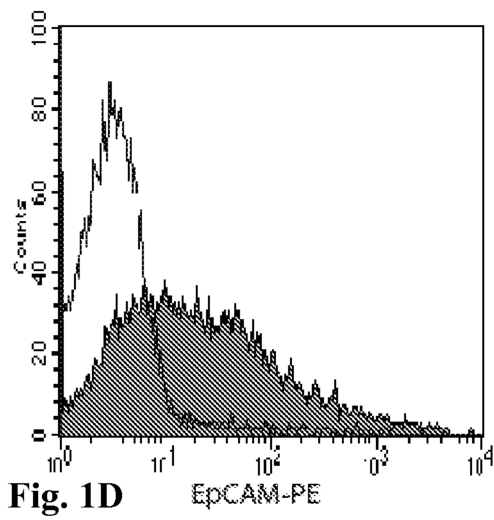
(FIG. 1B) Expression of the Epithelial Cell Adhesion Molecule EpCAM measured cytometry.
Figure 1C:
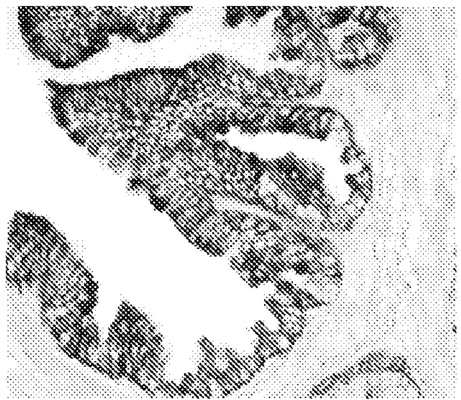
(FIG. 1C-D) Expression of cytokeratins in the IGR-CaP1 cell lines was measured by immunohistochemical labeling with anti-pan cytokeratin antibody (APK) in the initial tumor (C) and in the IGR-CaP1 cells at passage 16 (FIG. 1D). Photographs were 40×.
Figure 1D:
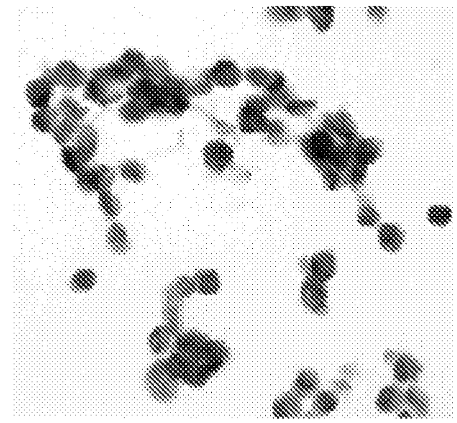

IGR-CaP1, a novel human prostatic cell line, was established from localized prostate tumour of a man treated by radical prostatectomy. From three localized tumour cultured of the natural extracellular matrix, one primoculture grow on the matrix during at least 10 passages. These cells were spontaneously immortalized since these cells are able to grow on plastic dishes in classical culture medium and they retained their proliferative capacity over a continuous long-term culture. They grew as adherent cells with epithelial cell morphology (FIG. 1A) and expressed the epithelial cell adhesion molecule EpCAM (FIG. 1B). They also stained positively for cytokeratin (FIG. 1C-D) as observed in the original tumour, confirming the epithelial origin of this cell line. The absence of chromogranin A expression in IGR-CaP1 cells lead us to rule out the hypothesis of neuroendocrine cells while the absence of the mesenchymal markers STRO-1, CD73 et CD105 and culture conditions used to establish the cell line suggested that these cells did not correspond to mesenchymal cells.

Figure 2A:
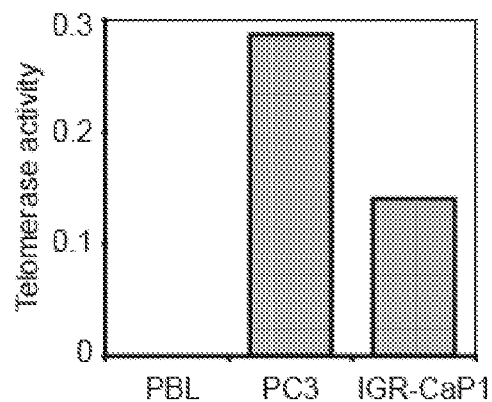
(FIG. 2A) The telomerase activity was quantified using a quantitative system in which extension products of telomerase are measured by quantitative PCR. The spontaneously immortalized IGR-CaP1 cells showed a high telomerase activity compared to normal lymphocyte cells (PBL), PC3 cells were used as positive control.
Figure 2B:
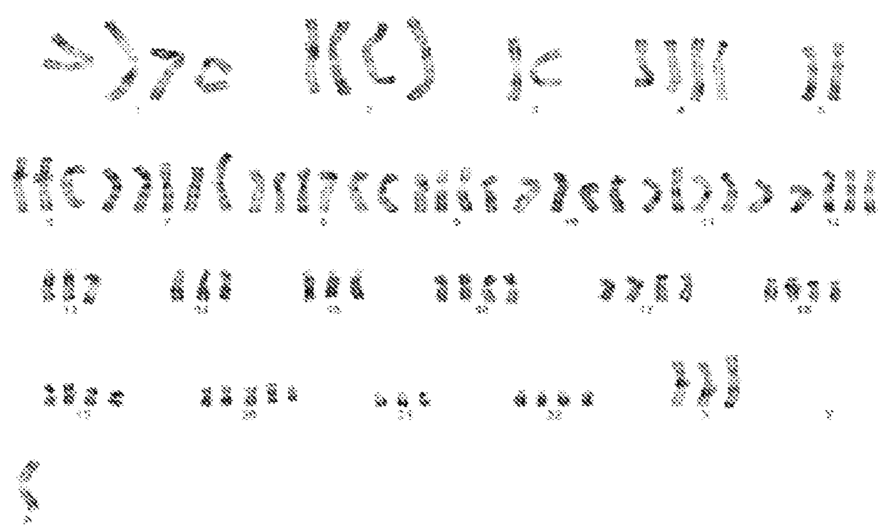
(FIG. 2B) Karyotypic analysis of the IGR-CaP1 cell by using a conventional G-banding technique showing a complex tetraploid karyotype with 86-91 chromosomes.

IGR-CaP1 Cells Spontaneously Expressed High Telomerase Activity and Showed Tumorigenic Features In Vitro Telomerase, the enzyme responsible for replicating telomeres, is expressed at low level in most normal tissues and became activated during tumorigenesis. It's now known that telomerase expression can itself induce immortalization. Because of the lack of prostate cancer model derived from a primary tumor, ectopic telomerase expression with retroviral vectors had been used to successfully immortalize human prostate epithelial (HPE) cells to artificially generate prostate cancer cellular models. To measure the telomerase activity in the IGR-CaP1 cell extracts, the inventors used a quantitative system in which extension products of telomerase are measured by quantitative PCR. The spontaneously immortalized IGR-CaP1 cells showed a high telomerase activity compared to normal lymphocyte cells (PBL) (FIG. 2A). This telomerase activity was however lower than telomerase activity measured from the PC3 prostate cell line derived from a metastatic localization. Karyotypic analysis was performed on the IGR-CaP1 cell line at passage 29 by using a conventional G-banding technique (FIG. 2B). The analysis showed a complex tetraploid karyotype with 86-91 chromosomes (FIG. 2B). The karyotype was determined to be 86~89 <4n>,XX,+der(X),+der(X),−Y,−Y, der(1)t(1;?)(p32;?), add(2)(q3?2),−3, der(3)t(3;?)(p10;?),−4,−4,−5,−5,−6,−6,ins(7;?)(p15;?),+8,+8,+11,+11,−13,−13, add(13)(q31),−14,−15,−15,del(18)(q22),del(18(q22),+20,del(20)(q12),+del(20)(q12),+mar inc [cp15].

Figure 2C:
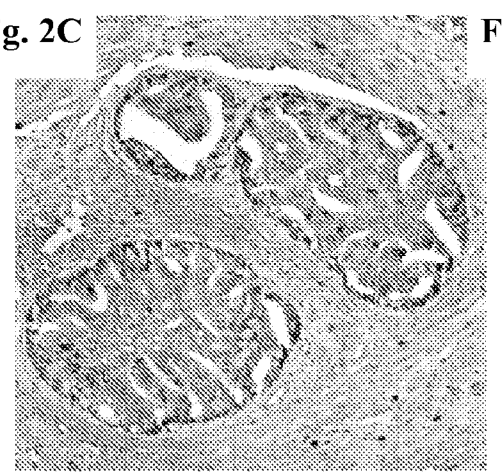
(FIG. 2C-D) Immunohistochemical analysis showing high p53 expression in the initial prostatic tumor (C) and in the derived-IGR-CaP1 cell line (D) leading to suspect mutations in the p53 gene.
Figure 2D:
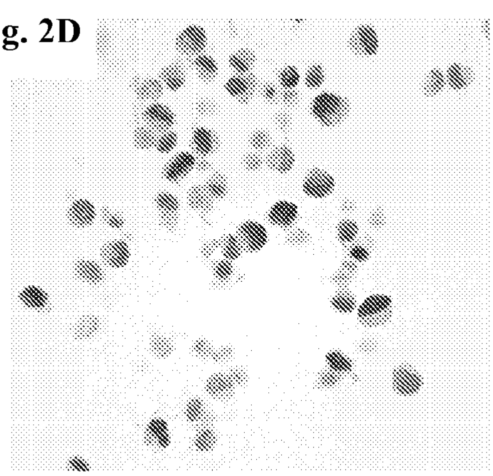

Since mutations in the tumour suppressor gene Tp53 are frequently associated with chromosome instability, expression of Tp53 was examined in the IGR-CaP1 cells. Immunohistochemical study showed a high expression of Tp53 protein in the parental tumour and in the derived cells (FIG. 2C-D). Tp53 expression in the IGR-CaP1 cell line was confirmed by western blot analysis with the anti-Tp53 DO-7 antibody. High expression of Tp53 was assumed to be corresponding to stabilized mutated Tp53 gene product. A single mutation in the nucleotide A377G was indeed detected by sequencing, corresponding to codon Y126C change.

Establishment of a Docetaxel-Resistant Derivative of the IGR-CaP1 Cell Line

IGR-CaP1-R100 cell line is an in vitro cellular model of prostate cancer resistant to docetaxel established by the inventors. In order to prepare this resistant cell line, IGR-CaP1 cells have been treated with a dose escalation of docetaxel as disclosed in Patterson et al (2006) (FIG. 3).

The survival and proliferation capacity in presence of docetaxel has been checked for IGR-CaP1-R cells by cellular cycle measurement (FIG. 4). Sensitive IGR-CaP1 cells (FIG. 4A) are blocked in G2-M phase when contacted with 100 nM of docetaxel for 48 h (FIG. 4B). IGR-CaP1-R100 cells which are resistant to 100 nM of docetaxel (FIG. 4C) cycle like the sensitive cells in absence of docetaxel. Contrary to the sensitive cells, the resistant cells are not blocked in G2-M phase in presence of docetaxel for 48 h (FIG. 4D). Same results have been obtained with IGR-CaP1-R cells resistant to other dose of docetaxel (e.g., 12 nM). These results show that IGR-CaP1-R cells acquired a real resistance against docetaxel.

IGR-CaP1 Cells Identification by Gene Profiling Analysis

Figures 5, 6:
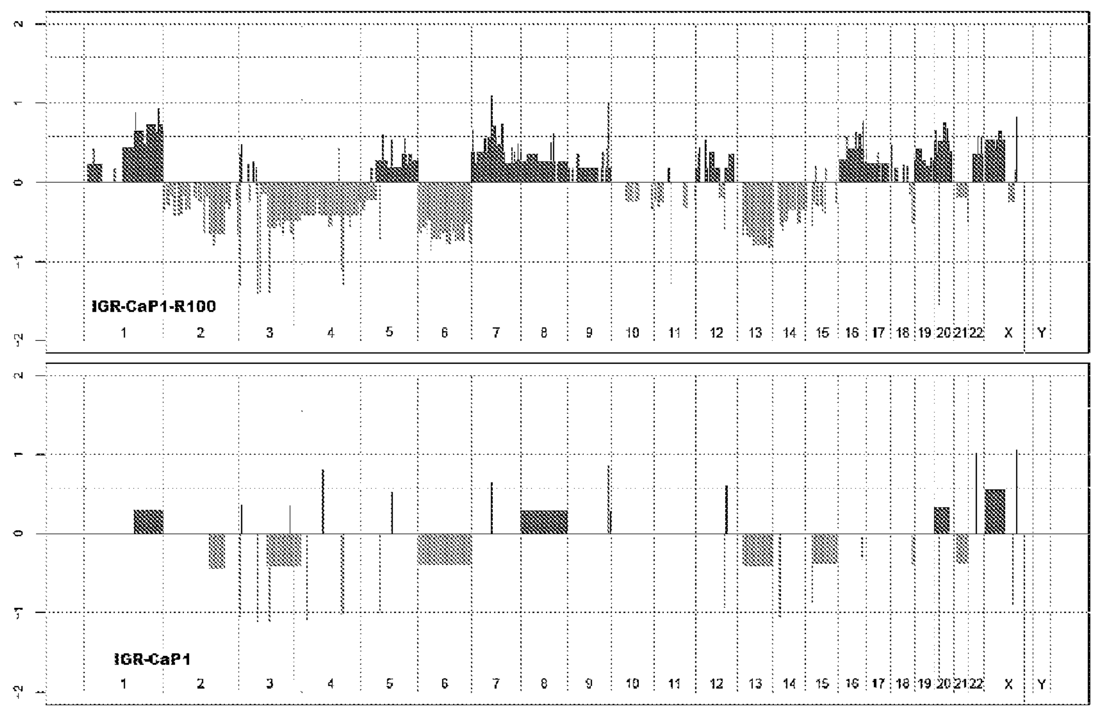
FIG. 5: STR profiles of IGR-CaP1 cell line and IGR-CaP1-R100 cell line. The new tags appearing in the resistant cell line are underlined.
FIG. 6: CGH array profiles of IGR-CaP1 cell line and IGR-CaP1-R100 cell line. The figure shows the profiles of the log 10Ratio for each chromosome.

In order to more characterize the cell line, the complete STR genotyping profile had been realized from total DNA of the IGR-CaP1 cell line and of the IGR-CaP1-R100 cell lines (FIG. 5). STR genotyping of cell lines is become a necessity for indisputably characterizing a cell line. This technique is rapid and can be carried out in any laboratory. For instance, the STR profile for 9 of the 16 analyzed loci is given in an increasing number of cell lines at the American Tissue and Culture Collections (ATCC). The profiles confirmed the complexity of the karyotype and showed the absence of chromosome Y on the amelogenin locus. The loss of the entire Y chromosome had been confirmed by the whole Y chromosome STR profile. The alleles 9.1/10.1/10.3/11.2 were shown to be rare at locus D7S820 in the whole population data bases. The inventors also found allele 9.1/10.3 for this locus in LNCaP cells on the STR data bank web site (http://www.cstl.nist.gov/div831/strbase/). The inventors observed the same STR profile between DNA prepared from IGR-CaP1 cells at passage 10 and DNA prepared from cells at passage 50, showing that chromosome alterations were conserved during the culture. During the resistant phenotype acquisition, 10 loci remained unchanged in the two cell lines and 6 loci were modified. Some rare alleles have been found in locus D7S820 (9.1, 10.1, 11.2).

In addition, in order to better characterize the modifications occurring during the resistant phenotype acquisition at the genomic level, a CGH profile of all chromosomes were carried out by CGH array of Agilent technologies Inc (FIG. 6). Both cell lines showed a similar global profile, proving their common origin. However, the resistant cell line presents a number of larger chromosomal aberrations with higher amplitude than the sensitive cell line, in particular on chromosomes +1q, −6, +7, −13 and +20. Two new events appear to be linked to the resistant phenotype acquisition, namely a gain of high amplitude on chromosomes 7 and 20.

Cell Growth and Kinetics of IGR-CaP1 Cells

Figure 7A:
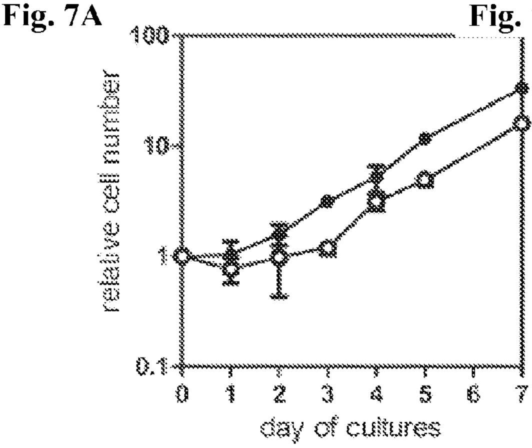
(FIG. 7A) The growth rate of IGR-CaP1 cells at passage 33 was determined with medium supplemented with 10% FCS (black filled) or with medium supplemented with charcoal-stripped serum.
Figure 7B:
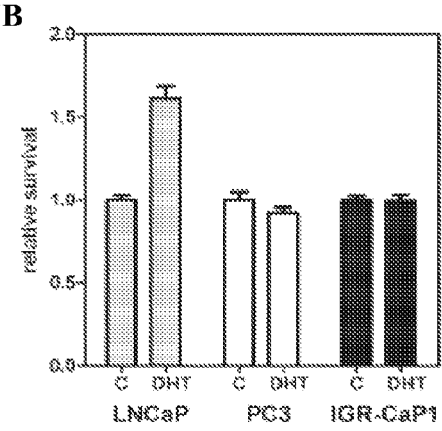
(FIG. 7B) The survival of IGR-CaP1, LNCaP and PC3 cells was determined after a treatment of 10-9M DHT for 72 hours compared to no treatment (FIG. 7C) in phenol red free-medium supplemented with charcoal-stripped serum. The figure shows the independence of the presence of androgen for the growth of IGR-CaP1 cells. The doubling time of IGR-CaP1 cells was 1.8 days.

The IGR-CaP1 cells grew rapidly in classical culture medium conditions with a doubling-time of 1.8 days. Same cellular kinetics was observed in medium containing charcoal-stripped serum (FIG. 7A). Treatment of cultured IGR-CaP1 cells in the presence of androgen DHT did not affect the cellular growth, as also observed for androgen-independent PC3 cells. As control, cellular growth of LNCaP cells was increased in a treatment of cells with 10-9M DHT for 72 hours (FIG. 7B).

IGR-CaP1 Cells do not Express AR Nor PSA

Figure 8A:
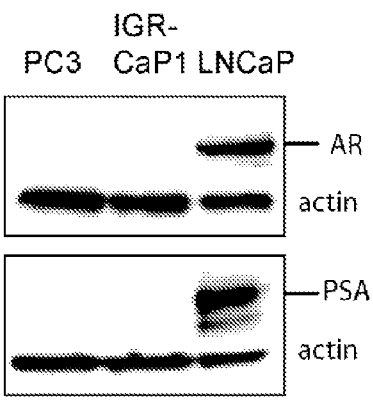
(FIG. 8A) Western blot analysis on whole cell extracts showed the absence of expression neither of the androgen receptor protein (AR) nor of the secretory prostate-specific antigen (PSA) in the IGR-CaP1 cells compared to PC3 as negative control and LNCaP cells as positive control.
Figure 8B:
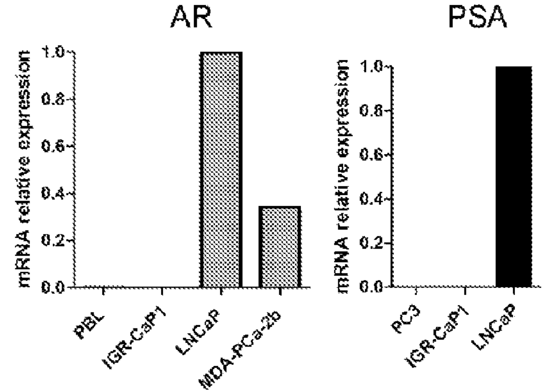
(FIG. 8B) Absence of AR and PSA expression was confirmed at the mRNA level by quantitative RT-PCR analyses in comparison with mRNA extracted from LNCaP or MDA-PCa-2b cells as positive controls and PC3 cells as negative control.

IGR-CaP1 cells did not express androgen receptor protein (AR) or secretory prostate-specific antigen (PSA) as shown by western analyses on whole cell extracts (FIG. 8A). AR protein was not observed even when cells were cultured in the presence of androgen. The LNCaP and MDA-PCa-2b cell lines that both expressed these two prostate-specific markers were used as positive controls; the androgen-independent PC3 cell line was used as negative control. Furthermore, neither AR nor PSA were detected at mRNA levels in IGR-CaP1 cells by real-time quantitative RT-PCR analyses (FIG. 8B). The expression of androgen receptor and PSA in the IGR-CaP1 cell line contrast with that was observed in the initial tumour. In addition, flow cytometry was used to examine the expression of the prostate biomarkers PSMA and demonstrated the absence of this prostatic marker in the IGR-CaP1 cells. In the prostatic epithelium, expression of androgen receptor and PSA was restricted to luminal secretory prostate cells and was not observed in the cells that formed the basal layer of the epithelium, suggesting that the IGR-CaP1 cells might correspond to basal epithelial cancer prostate cells.

IGR-CaP1 Cells Reconstitute Prostate Adenocarcinoma in Mice that Recapitulates the Original Tumour Features To determine tumorigenicity of IGR-CaP1 cells in animals, cells were injected into male nude mice both subcutaneously and intraprostatically. Subcutaneous injection of IGR-CAP1 cells resulted in the formation of palpable tumors within a week and 90% of mice (20/22) were bearing 7-9 mm tumours after 6-8 weeks. One mouse developed intraperitoneal ascites without subcutaneous tumour. Intraprostatic injection of IGR-CaP1 cells resulted in the formation of intraprostatic tumors in 38% of mice (5/13). The serum samples of tumor-bearing mice contained no measurable PSA. HES-staining section of the tumours revealed a glandular differentiation with ascini attesting the presence of adenocarcinoma (FIGS. 9A and 9B). Immunohistochemical staining of the tumours with Ki67 showed a high proliferation index which was higher in intraprostatic tumour. Cytokeratin staining proved the epithelial features and prostatic acid phosphatase (PAP) and PSMA staining attested from the prostate origin of the tumour (FIG. 9). A low AMACR (P504S) staining was also observed, higher staining was observed in intraprostatic tumour. Interestingly, vimentin staining was intense in subcutaneous tumours corresponding to that was observed in the parental IGR-CaP1 cells but it was absent in intraprostatic tumours. Vimentin is considered to be the intermediate filament of mesenchymal tissue. The aggressive character of the subcutaneous tumours was variable: some tumour-bearing mice showed necrosis and fibrosis in involutive forms with no more tumour features. In contrast, some mice showed aggressive tumours that infiltrate the whole peritoneal cavity, forming ascites, and including kidney, spleen and pancreas. Predominant metastases were observed in liver and in lung (FIG. 9C). Intraprostatic tumours were always aggressive and showed metastasis in the diaphragm including kidney and liver and micrometastasis in lung. Collectively, these data showed that intraprostatic tumour initiated by the IGR-CaP1 cell line recapitulates in mice the characteristics of the initial undifferentiated human prostate tumour. Tumour grade and metastasis localization corresponds to that was observed for patient presenting undifferentiated tumour with a high-Gleason score.

IGR-CaP1 Cells Express High Levels of Basal Epithelial Prostate Markers.

To determine if IGR-CaP1 cells show basal, luminal or intermediate cell phenotypes, the expression of cytokeratin markers CK5, CK8, CK14 and CK18 were first examined by cytometer analysis (FIG. 10). Cytokeratin expression profile of luminal epithelial prostate LNCaP cell line was used as control. IGR-CaP1 cells exhibit strong staining for CK5/8 and CK14 but absence of staining for CK8. Although adult prostate basal cells were shown to express p63, the inventors did not detect p63 expression in these cells. They detected a low labelling for the luminal epithelial marker CK18 in IGR-CaP1 cells compared to that observed in LNCaP cells. Absence of CK8 and low level of CK18 expression indicated the absence luminal differentiation in culture of IGR-CaP1 cells. Additionally, CK19 expression was detected in early passage of the IGR-CaP1 cell line, but disappeared with culture passage and was not detectable in cells at passage 71. The two IGR-CaP1 clonally-derived clones 3A11 and 3C11 showed roughly the same cytokeratin expression profile. Collectively, these results showed that the IGR-CaP1 cell line showed cytokeratin profile expression corresponding to basal epithelial cells. Furthermore, as prostate stem cells were shown to exist in the basal cell compartment, these data suggested that a low subset of these cells expressing a broad spectrum of cytokeratin profile might correspond to progenitor/stem cells.

IGR-CaP1 Cells and Clonally-Derived Clones Showed Features of Prostate Cancer Stem Cells.

The basal cells are particularly important as the basal cell compartment is thought to contain the epithelial stem or progenitor cells. Cancer stem cells possess the intrinsic stem cell properties of renewal, proliferation and differentiation. However it is assume that these cells are responsible for initiating cancer growth, it is still difficult to draw up the molecular profile that defines a prostate cancer stem cell. In the prostate, the putative stem cell population was enriched using the CD44 and CD133 antigens. Therefore, the inventors first evaluated CD44 and CD133 expression levels within IGR-CaP1 cell line by flow cytometry (FIG. 11A). Compared to LNCaP cells in which only a minor fraction of cells expressed CD44, almost all the IGR-CaP1 cells expressed CD44 antigen. Indeed, CD133 expression was not observed in LNCaP cells. In contrast, the inventors detected two populations in IGR-CaP1 cells, one population showing a high expression of CD133 and a CD133-negative fraction. CXCR4 is a key molecule in the regulation of the migratory and metastatic properties of cancer cells. Recent data suggested that the CXCR4 axis may be essential for the progression of the CD133+ prostate cancer stem cells. The inventors found that a large subset of IGR-CaP1 cells express CXCR4 molecule. Gene expression of CD133 and CXCR4 were measured by real-time quantitative RT-PCR in the parental IGR-CaP1 cell line and in the clonally-derived clones 3A11 and 3C11 (FIG. 11B). All the cells showed a high expression of these two stem cell markers, CD133 was two fold less expressed in 3A11 cells while 3C11 cells conserved a high expression of CD133. The inventors next evaluate the combination of the biomarkers expression after triple-labelling and analysis by flow cytometry. In the parental IGR-CaP1 cell line, the CD44+/CD133+/CXCR4+ cells represented 13% expression. The fraction of triple-labelled cells was highly increased in derived clones as the inventors observed 23% and 34% of CD44+/CD133+/CXCR4+ cells in 3A11 and 3C11 clones respectively. They next evaluated the ability of $CD44^{+}$/$CXCR4^{+}$/$CD133^{+}$ sorted cells to differentiate under 3D differentiating conditions (FIG. 13). Among CD133 negative cells, they observed no difference in the differentiation ability between CRCR4+ and CXCR4− cells. However in CD133 positive cells, CXCR4− cells keep their differentiation capacity while CD133+/CXCR4+ lost most of their morphologic differentiation potential. Under stem cells conditions CD133+/CXCR4+ and CD133+/CXCR4− cells produced the same spheroid structures on matrigel.

IGR-CaP1 Cells Showed a Stem Cell Marker Expression Signature.

It has been established that the phenotype $\alpha2\beta1^{hi}$/CD133+ determines normal prostate epithelial stem cells. IGR-CaP1 and clonally-derived clones were stained for expression of α2β1 integrin. All cells contained two type of population, some cells highly expressed α2β1 integrin whilst another population showed a very low expression (FIG. 12A). The inventors observed high expression of CD133 and α2β1 integrin in the IGR-CaP1 cell line and the two derived clones 3A11 and 3C11, suggesting the existence of a large subset population of cells exhibiting the characteristics of stem cells, and possibly corresponding to stem cells.

The inventors next explored if other signalling pathways implicated in stemness could be activated in our model. The transcription factor Oct4 is expressed in pluripotent embryonic stem (ES) and germ cells and is currently considered a main regulator of human embryonic stem cell pluripotency and self-renewal capacities. Oct 4, Nanog and Sox2 have been shown to be expressed in HPET immortalized prostate cancer cells that were shown to reconstitute the original human tumor in vivo and had been suggested to constitute an in vitro model for prostate cancer stem cells. Microarray analysis realized on the IGR-CaP1 cells revealed gene expression of Oct4. Western blot analysis confirmed the expression of Oct4 in IGR-CaP1 cells, contrasting to the control LNCaP and PC3 cells (FIG. 12B). Because the Hedgehog (Hh) and Notch signalling pathways regulate key functions of stem/progenitor cells self-renewal, the inventors next used real-time RT-PCR to assess their expression (FIG. 12C). They observed a marked increase of expression of several stemness markers in IGR-CaP1 cells compared to the control LNCaP cells. Sonic Hedgehog (SHH) which has been implicated in signalling in the maintenance and/or proliferation of prostatic progenitor cells was the most expressed gene. Several recent observations are consistent with a role for Hedgehog (HH) pathway in carcinogenesis. To confirm SHH pathway activation, the inventors assess the expression of the HH receptor Patched protein (PTCH1) and GLI target gene products. They observed an increase in both GLI1 and GLI2 target gene expression supporting an activation of the Hedgehog pathway in IGR-CaP1 cells. A role for Notch as a marker and regulator of normal prostate stem/progenitor cells, however, has only recently been suggested although there is currently still little evidence to support Notch as a marker of prostate cancer stem/initiating cells. LNCaP cells were reported to express Notch1 at mRNA and protein levels. In IGR-CaP1 cells, Notch1 mRNA was expressed at roughly 3 fold higher than in LNCaP cells. IGR-CaP1 cells also expressed high level of mRNA coding for the breast cancer resistance protein BCRP/ABCG2 which has been implicated in tumorigenic stem-like cancer cells enriched-side population.

IGR-CaP1 Induced Intensive Bone Remodeling after Direct Injection in Bone

Bone metastases are common in advanced prostate cancer and are associated with significant morbidity, including pain. Bone metastases from prostate cancer usually form osteoblastic or mixed lesions.

Figure 14A:
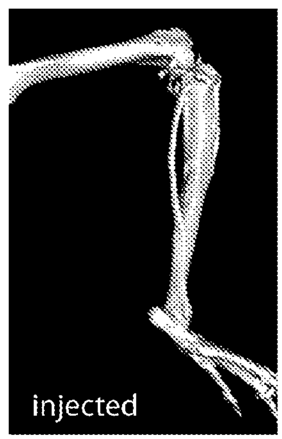
Figure 14B:
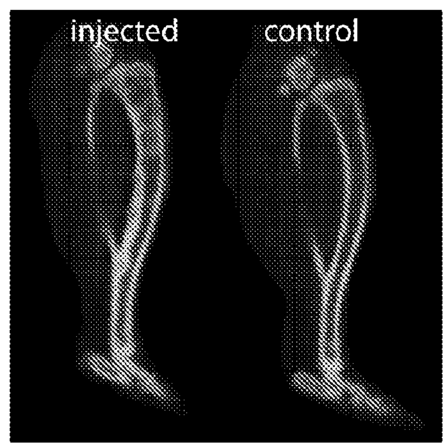
Figure 14C:
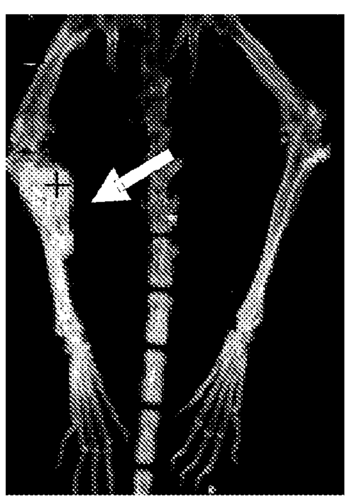
Figure 14D:
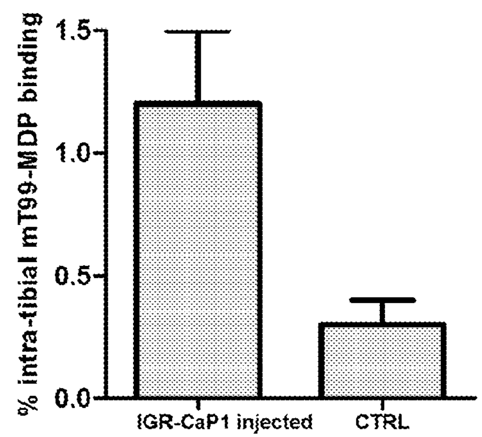
Figure 14E:
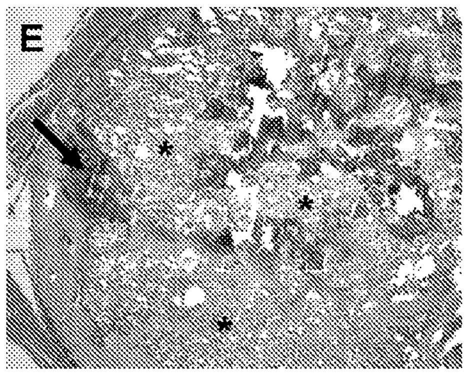
Figure 14F:
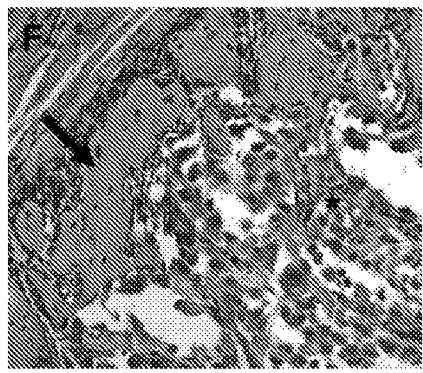

Changes in bone density and micro-architecture were analyzed in mice by using high resolution XCT, 10 weeks after direct IGR-CaP1 cells injection in bone. The same images showing both osteolytic lesions and bone formation were observed in 86% of injected mice (6/7) (FIGS. 14A and 14B). 3D radio-isotope imaging with high-resolution SPECT/X CT is like bone scintigraphy performed in humans based on 99 m Technetium-Methylenediphosphonate (99 mTc-MDP) uptake. It allows the inventors to quantify bone remodeling induced by IGR-CaP1 tumor cells. The bone remodeling was assessed by 99 mTc-MDP SPECT/CT on 6 mice, 21 weeks after direct injection of IGR-CaP1 cells in bone. An intensive bone remodeling in injected tibias compared to control was clearly showed (FIGS. 14C and 14D). These results confirmed the bone modifications observed by CT. Analysis of HES-stained sections showed that the intratibial tumors had invaded both the total bone marrow cavity and outside the bone (FIGS. 14E and 14F) with multiple areas of bone osteogenesis and reactive new bone formation. These results showed that IGR-CaP1 cells induced both osteoblastic and osteolytic lesions in bone with important bone remodelling and predominance of osteoblastic lesions thus reconstituting an appropriate model to evaluate the therapeutic response of new bone-targeting drugs in prostate cancer.

Materials and Methods

Clinical Summary

Prostate tissue was obtained from a 58-year-old caucasian-french patient who underwent a radical prostatectomy for clinically localized prostate cancer. The patient had a PSA of 5.6 ng/ml and a free-PSA of 6%. Subsequent pathological evaluation revealed a massive bilateral posterior tumour limited to the prostatic capsule and was diagnosed as a moderately differentiated adenocarcinoma with a Gleason score of 7 (4 (70%)+3 (30%)). Clinical staging was assessed as pT2c Nx.

Cell Culture

Prostate tissues were obtained from 3 patients undergoing radical prostatectomy for localized prostate cancer. Fresh prostatectomy specimens were obtained under sterile conditions. After a mechanic dissociation of the tumour tissue, cells were counted and seeded on the natural extracellular matrix in RPMI medium supplemented in 10% FBS (Gibco), penicillin-streptomycin antibiotics and fungizone. This natural extracellular matrix has been developed by J. Bénard in the Gustave Roussy Institute to increase chance of obtaining rare cell lines. The RPMI medium used for primocultures was depleted in proline amino acid to eliminate fibroblast contamination. The cells were incubated at 37° C. at 5% CO2 until reaching semi-confluency. The culture was pursuing on the extracellular matrix until 10 to 20 passages and then, was continuing in classical RPMI medium containing 10% FBS and antibiotics on plastic dishes. Others prostate cancer cell lines were cultured as previously described: LNCaP and PC3 cells were grown in RPMI medium containing 10% FBS and MDA-PCa-2b cells were grown in BRFF-HPC1 medium completed with 20% FBS and 50 μg/ml gentamycin.

Cell Growth Kinetics

The cell growth kinetic was determined by counting the viable cell number at regular intervals. Cells were seeded in triplicate at 4000 cells/well in 12 well plates in normal culture medium or in medium containing 10% of charcoal-stripped serum. Each day, cells were colored with trypan blue and counted. The doubling-time was calculated from regression equation of the curve. For the hormone-dependent growth assay, cells were seeded at 10 000 cells/well in 96 well plates. After 24 h, the culture medium was replaced with medium without phenol red containing 10% of charcoal-stripped serum and the DHT was added or not at the final concentration of $10^{-9}$M. The medium was replaced each day. After 72 hours, cell survival was measured with the WST1 test according the manufacturer's procedures.

Cell Cycle Analysis

Freshly plated IGR-CaP1 and IGR-CaP1-R100 cells were incubated for 48 h in complete medium containing or not 100 nM of docetaxel. Cell cycle distribution was studied on 70% cold ethanol-fixed cells, by propidium iodide staining (50 μg in PBS) and RNAse treatment (20 μg) followed by flow cytometry analysis (FACScalibur Becton-Dickinson).

Telomerase Assay

A highly sensitive in vitro assay based on quantitative real-time telomeric repeat amplification protocol has been used for detecting telomerase activity (QTD Kit, BioMax, Inc.). The telomerase activity is determined through its ability to synthesize telomeric repeats onto an oligonucleotide substrate in cellular extracts and resulting extended products were amplified by PCR (35-40 cycles) using the DNA fluorochrome SYBR Green.

Cytogenetic Analysis DNA Sequencing for Analysis of TP53 Mutation

Genomic DNA was extracted from cultured cells and was amplified using the TP53-specific primers 5'-ATTTGATGCTGTCCCCGGACGATATTGAA-3' (exon 3) (SEQ ID No. 1) and 5'-CACTCCAGCCACCTGAAGTCCAAAAAGGGT-3' (exon 10) (SEQ ID No. 2). PCR products amplification was verified by electrophoresis and amplified DNA was sequenced on an automatic sequencer (Applied Biosystems 3730). Two different DNA preparations obtained from different cell aliquots showed the same TP53 mutation.

Karyotype

Metaphases were harvested after a 2.5-hour colchicine block. Chromosome spreads were obtained according to previously described techniques. Karyotypes were established after R-banding.

STR Typing

Genomic DNA was prepared from the cells using kit QIAamp DNA Micro kit (Qiagen). Human genomic DNA was quantified using sensitive real time PCR technology, using human specific primers and hydrolysis probes. Q-PCR was performed on LightCycler480 Instrument, (Roche) and analyzed with LightCycler480 software 1.5.

STR analysis was conducted using the multiplex-PCR-based Identifiler® amplification kit (Applied Bio systems). Fluorescent STR-based amplification was conducted with 1 ng of human genomic DNA. 15 autosomal STR Loci were simultaneously co-amplified, including D8S1179, D21511, D7S820, CSF1P0, D3S1358, TH01, D135317, D165539, D2S1338, D195433, vWA, TPDX, D18551, D5S818 and FGA plus the Amelogenin gender-determining marker. Automated DNA fragment Analysis was performed by electrophoresis on ABI3130x1 Genetic Analyser (Applied Biosystems). Fluorescent data were collected and analyzed using GeneMapper 3.2 ID specific genotyping software (Applied Biosystems). The resulting profile showed the assigned allele values corresponding to the number of repeat units identified for each locus.

Array Comparative Genomic Hybridization

Genomic DNA was purified with QiaAmp DNA kit (Qiagen) according to the manufacturer's instructions. DNA was hybridized to 244K human CGH Agilent arrays (G4411B). DNA labeling, dye-swap hybridization, and washing procedures were performed according to the manufacturers' recommendations. Control DNA was purchased from Promega (Human Genomic DNA male). The chips were scanned on an Agilent G2565BA DNA Microarray Scanner and image analysis was done using the Feature-Extraction V10.1 software (Agilent Technologies). Feature-Extraction was used for the fluorescence signal acquisition from the scans. Raw copy number ratio data were transferred to the CGH Analytics v3.4.40 software for further analysis. Aberrations were defined with ADM2 method for segmentation with threshold 10, Log 2ratio>0.15 and number of probes ≥5.

In Vivo Tumorigenicity Assay

Male athymic nude mice (NC-nu/nu) of 6-7 week old were used to carry out tumorigenicity assay. All of the operative procedures and animal care were in conformity with the Guidelines of the French Government. Subcutaneous injections were realized into the dorsal side with $10^7$ viable IGR-CaP1 cells in 100 μl of PBS (lacking matrigel). Orthotopic injections were realized as previously described (Fizazi et al., 2004). Briefly, the prostate of each anesthetized mouse was exposed through a midline laparotomy incision and direct injection into the prostate was performed with $10^6$ cells in 5 μl PBS.

Western Blot Analysis

Western blot assays were performed on 50 μg of whole cellular lysates loaded on pre-casted 4-12% NuPage gels (Invitrogen). Blots were probed with the following antibodies: rabbit polyclonal anti-androgen receptor antibody (AR) (N-20, Santa Cruz), goat polyclonal anti-PSA antibody (C-19, Santa Cruz), rabbit anti-Oct4 antibody (Chemicon) Anti-rabbit (Pierce) or anti-goat (Dako) IgG-horseradish peroxidase antibody served as the secondary antibody. Immunoblot analyses were developed using the enhanced chemoluminescence-based detection kit (Pierce, Rockford, Ill., USA).

Flow Cytometry

Fluorescence-activated cell sorting (FACS) analysis was used for determination of differentiation marker expression and cell sorting. For cytoplasmic or nuclear proteins, a permeabilization in 0.25% triton X-100 was performed before labelling. The following antibodies were used: anti-human EpCAM-PE (clone EBA-1, Becton Dickinson), PSMA-FITC (clone 107-1A4, MBL medical), CK5/8-FITC (clone 5F173, US Biological), CK8-FITC (clone B22.1, GeneTex, Inc.) et CK14-FITC (Clone 2Q1030, US Biological), CD44-FITC (Clone G44-26, BD Biosciences), CD133-APC (AC133, Miltenyi Biotec) et CXCR4-APC (CD184 clone, BD Pharmingen). For three-color staining analysis, CD184-PE (CD184 clone, BD Pharmingen) was used. The corresponding isotype control antibodies were included in each staining condition. Samples were analyzed with FACSCalibur cytometer (Becton Dickinson). Triple-color stained cells were sorted by cell sorter (MoFlo-Dako).

TaqMan Real-Time Quantitative Reverse Transcription-PCR Analysis.

Total RNA was extracted from tumor cell lines using the RNeasy Midi kit (Qiagen) according to the manufacturer's protocol. One μg of RNA was reversed transcribed using random hexamers according to the manufacturer's recommendations (Applied Biosystems). Quantitative real-time PCR was performed using 5 μl of diluted cDNA (1 μl in 19 μl of water) in a final volume of 25 μl according to the manufacturer's recommendations (Applied Biosystems). PCR primers and probe for the target genes androgen receptor ( ) and PSA, were designed by Applied Biosystems and used according to the manufacturer's recommendations. In each experiment, the amount of sample RNA was normalized by the amplification of an endogenous control (18S). The relative quantification of the transcripts was derived by using the standard curve method (Applied Biosystems User Bulletin 2, ABI PRISM 7700 Sequence Detection System).

Immunohistochemistry

The different specimens (primary tumors and potential tumour organs) from mice studied in 3 experiments were fixed in Finefix (Milestone Medical), and then paraffin sections (4 μm thick) and hematoxylin-eosin-saffranin (HES) slides were prepared. For immunohistochemistry, tumor and organ sections were incubated with anti-pan-CK (Pan Ab-2, LabVision), anti-p53 (Ventana Medical Systems), anti-PSMA (clone 3E6, Diagnostic BioSystems), anti-PAP (PSAP clone PASE/4LJ, Diagnostic BioSystems), anti-AMACR (P504S, Diagnostic biosystems), anti-Ki67(-Zymed), anti-vimentin (Clone V9, Sigma) antibodies. All of the sections were analyzed by using a Zeiss Axiophot microscope and a SensiCam PCO digital camera. Representative views were taken at a magnification of 100×.

Immunofluorescence Microscopy

Cells were seeded on sterile glass coverslip. When cells reached to 80% confluence, they were fixed at room temperature in 4% formaldehyde in PBS buffer for 10 min and then washed five times in PBS. Cells were permeabilized for 10 min in a 0.25% Triton X-100 and extensively washed, and blocked in a 1:100 normal goat serum solution (Sigma). The coverslips were incubated with primary antibody anti-human $\alpha 2\beta 1$ integrin (clone BHA2.1, Chemicon) for 1 hour at room temperature followed by a 30 min with Alexa Fluor 488 goat antimouse secondary antibody (Molecular Probes). Nuclei were stained with Dapi vectashield mounting reagent (Vector Laboratories). Images were acquired on a Zeiss Axioplan 2microscope.

Intrabone Injections and 3D Imaging

Male nude mice (NC-nu/nu) were anesthetized with isofurane inhalation. Aliquots of $5\times10^5$ IGR-CaP1 cells were diluted in 20 μl of PBS and then injected into the right tibia of each of 7 mice using a 500 μl insulin needle. The contralateral tibia was used as an internal control. Ten weeks after bone injection, the anaesthetized mice were monitored by X-rays CT using eXplore Locus (General Electric, USA). Eleven weeks later, in vivo imaging was performed with a Nano-SPECT/CT (Single-Photon Emission Computed Tomography/Computerized Tomography) small-animal imaging system (Bioscan, Washington, D.C., USA). Eighteen MBq of [99 mTc] MDP (Methylene Di Phosphonate) was injected intravenously, and 1 hour after, SPECT/CT imaging was performed on anaesthetized animals. After acquisition of a CT topogram, the region for scanning acquisition was defined (typically full body to visualize the entire skeleton). Then, a SPECT was performed (30 to 60 sec acquisitions, 24 projections) then a CT scan was acquired. The absolute activity was analyzed in both legs with volume of interest drawn around the tumor, and expressed as percentage of injected dose.

REFERENCES

Attard G, et al. A novel, spontaneously immortalized, human prostate cancer cell line, Bob, offers a unique model for pre-clinical prostate cancer studies. Prostate 2009; 69:1507-1520.

Daly-Burns B, et al. A conditionally immortalized cell line model for the study of human prostatic epithelial cell differentiation. Differentiation. 2007 January; 75(1):35-48.

Erten C, et al. Regulation of growth factors in hormone- and drug-resistant prostate cancer cells by synergistic combination of docetaxel and octreotide. BJU Int. 2009 Feb. 3.

Fizazi K et al. High efficacy of docetaxel with and without androgen deprivation and estramustine in preclinical models of advanced prostate cancer. Anticancer Res 2004; 24:2897-2903

Gu Y, et al. A telomerase-immortalized primary human prostate cancer clonal cell line with neoplastic phenotypes. Int J Oncol. 2004; 25: 1057-1064.

Gu G, et al. Prostate cancer cells with stem cell characteristics reconstitute the original human tumor in vivo. Cancer Res. 2007; 67: 4807-4815.

Koochekpour S, et al. Establishment and characterization of a primary androgen-responsive African-American prostate cancer cell line, E006AA. Prostate 2004; 60: 141-152.

Kucukzeybek Y, et al. Enhancement of docetaxel-induced cytotoxicity and apoptosis by all-trans retinoic acid (ATRA) through downregulation of survivin (BIRC5), MCL-1 and LTbeta-R in hormone- and drug resistant prostate cancer cell line, DU-145. J Exp Clin Cancer Res. 2008; 27:37.

Litvinov I V, et al. Low-calcium serum-free defined medium selects for growth of normal prostatic epithelial stem cells. Cancer Res. 2006 Sep. 1; 66(17):8598-607.

Lo Nigro C, et al. The combination of docetaxel and the somatostatin analogue lanreotide on androgen-independent docetaxel-resistant prostate cancer: experimental data. BJU Int. 2008 Aug. 5; 102(5):622-7.

Makarovskiy A N, et al. Survival of docetaxel-resistant prostate cancer cells in vitro depends on phenotype alterations and continuity of drug exposure. Cell Mol Life Sci. 2002; 59: 1198-1211.

Miki J, et al. Identification of putative stem cell markers, CD133 and CXCR4, in hTERT-immortalized primary nonmalignant and malignant tumor-derived human prostate epithelial cell lines and in prostate cancer specimens. Cancer Res. 2007 Apr. 1; 67(7):3153-61.

Nomura T, et al. Expression of the inhibitors of apoptosis proteins in cisplatin-resistant prostate cancer cells. Oncol Rep. 2005 October; 14(4):993-7.

Patterson S G, et al. Novel role of Stat1 in the development of docetaxel resistance in prostate tumor cells. Oncogene. 2006 Oct. 5; 25(45):6113-22.

Sallman D A, et al. Clusterin mediates TRAIL resistance in prostate tumor cells. Mol Cancer Ther. 2007 November; 6(11):2938-47

Selvan S R, et al. Establishment and characterization of a human primary prostate carcinoma cell line, HH870. Prostate. 2005; 63: 91-103.

Shoemaker R H. The NCI60 human tumour cell line anticancer drug screen. Nature Rev. 2006, 6: 813-823.

Sowery R D, et al. Clusterin knockdown using the antisense oligonucleotide OGX-011 re-sensitizes docetaxel-refractory prostate cancer PC-3 cells to chemotherapy. BJU Int. 2008 August; 102(3):389-97.

Takeda M, et al. The establishment of two paclitaxel-resistant prostate cancer cell lines and the mechanisms of paclitaxel resistance with two cell lines. Prostate. 2007, 67:955-67.

van Bokhoven A, et al. Molecular characterization of human prostate carcinoma cell lines. Prostate. 2003; 57: 205-225.

Yasunaga Y, et al. A novel human cancer culture model for the study of prostate cancer. Oncogene. 2001; 20: 8036-8041.

What is claimed is:

1. An isolated prostate cancer cell line selected from:

a) a prostate cancer cell line designated IGR-CaP1 and deposited with the Collection Nationale de Culture de Microorganismes (CNCM) under deposit number I-4126 on Feb. 10, 2009 or a progeny thereof; or b) a prostate cancer cell line according to a) treated with a cytotoxic drug to produce a prostate cancer cell line resistant to said cytotoxic drug.

2. A composition comprising a cytotoxic compound and a prostate cancer cell line designated IGR-CaP1 and deposited with the Collection Nationale de Culture de Microorganismes (CNCM) under deposit number I-4126 on Feb. 10, 2009 or a progeny thereof.

3. The composition according to claim 2, wherein said cytotoxic drug is selected from docetaxel, paclitaxel, mitoxantrone, platin salts, doxorubicin, vinblastine, estramustine or etoposide.

4. A prostate cancer cell line resistant to 100 nM of docetaxel and designated IGR-CaP1-R100, deposited with the Collection Nationale de Culture de Microorganismes (CNCM) under deposit number I-4127 on Feb. 10, 2009, or a progeny thereof.

5. A method for preparing a prostate cancer cell line resistant to a dose of a cytotoxic drug comprising treating a prostate cancer cell line designated IGR-CaP1 and deposited with the Collection Nationale de Culture de Microorganismes (CNCM) under deposit number I-4126 on Feb. 10, 2009 or a progeny thereof with increasing amounts of a cytotoxic drug and selecting a resulting prostate cancer cell line resistant to the cytotoxic drug.

6. A kit comprising culture medium and a prostate cancer cell line selected from:

a) a prostate cancer cell line designated IGR-CaP1 and deposited with the Collection Nationale de Culture de Microorganismes (CNCM) under deposit number I-4126 on Feb. 10, 2009 or a progeny thereof; or b) a prostate cancer cell line resistant to 100 nM of docetaxel and designated IGR-CaP1-R100, deposited with the Collection Nationale de Culture de Microorganismes (CNCM) under deposit number I-4127 on Feb. 10, 2009, or a progeny thereof.

7. A method for determining whether a candidate agent inhibits proliferation of a prostate cancer cell line comprising: a) contacting a prostate cancer cell line designated IGR-CaP1 and deposited with the Collection Nationale de Culture de Microorganismes (CNCM) under deposit number I-4126 on Feb. 10, 2009 or a progeny thereof, or a prostate cancer cell line resistant to 100 nM of docetaxel and designated IGR-CaP1-R100, deposited with the Collection Nationale de Culture de Microorganismes (CNCM) under deposit number I-4127 on Feb. 10, 2009, or a progeny thereof, with a candidate agent; b) measuring the proliferation of the cell line so contacted; and c) determining if said candidate agent inhibits the proliferation of said prostate cancer cell line, wherein a reduction in proliferation indicates that the candidate agent inhibits proliferation of the prostate cancer cell line.

8. The method of claim 7, wherein the candidate agent is a chemical molecule, a polypeptide, a nucleic acid molecule, an antibody, a metal, a radiotherapy or a combination thereof.

9. A method for determining whether a candidate agent increases sensitivity of a prostate cancer cell line to a cytotoxic drug comprising: a) contacting a prostate cancer cell line designated IGR-CaP1 and deposited with the Collection Nationale de Culture de Microorganismes (CNCM) under deposit number I-4126 on Feb. 10, 2009 or a progeny thereof, or a prostate cancer cell line resistant to 100 nM of docetaxel and designated IGR-CaP1-R100, deposited with the Collection Nationale de Culture de Microorganismes (CNCM) under deposit number I-4127 on Feb. 10, 2009, or a progeny thereof, with a candidate agent in the presence of said cytotoxic drug; b) measuring the proliferation of the cell line so contacted; and c) determining if said candidate agent increases the sensitivity of said prostate cancer cell line, wherein a reduction in proliferation indicates that the candidate agent increases the sensitivity of the prostate cancer cell line to the cytotoxic drug.

10. The method of claim 9, wherein the proliferation of the cells in step b) is measured using a method selected from the group consisting of DNA cell cycle methods, $^{3}$H-thymidine incorporation, cell counts, colorimetric cell proliferation assays or efficiency of colony formation methods.

11. The method of claim 10, wherein the proliferation of the cells in step b) is measured using a method selected from the group consisting of $^{3}$H-thymidine incorporation, cell counts and colorimetric cell proliferation assays.

12. The method of claim 9, wherein the candidate agent is a chemical molecule, a polypeptide, a nucleic acid molecule, an antibody, a metal, a radiotherapy or a combination thereof.

* * * * *

UNITED STATES PATENT AND TRADEMARK OFFICE

CERTIFICATE OF CORRECTION

PATENT NO. : 8,674,172 B2
APPLICATION NO. : 13/264479
DATED : March 18, 2014
INVENTOR(S) : Anne Chauchereau et al.

It is certified that error appears in the above-identified patent and that said Letters Patent is hereby corrected as shown below:

In the Specification

Column 2,
Line 57, "number 1-4126" should read --number I-4126--.

Column 3,
Line 6, "number 1-4127" should read --number I-4127--.

Column 4,
Line 43, "log 10Ratio" should read --log10Ratio--.

Column 5,
Line 23, "CD 133" should read --CD133--.

Column 6,
Line 56, "1-4126" should read --I-4126--.

Column 7,
Line 2, "TPDX," should read --TPOX,--.
Line 4, "CSF1P0," should read --CSF1PO,--.
Line 5, "TPDX," should read --TPOX,--.

Column 17,
Lines 18-20, "99 m Technetium-Methylenediphosphonate (99 mTc-MDP)" should read --99mTechnetium-Methylenediphosphonate (99mTc-MDP)--.
Line 22, "99 mTc-MDP" should read --99mTc-MDP--.

Column 18,
Line 57, "(Applied Bio systems)." should read --(Applied Biosystems).--.

Signed and Sealed this
Third Day of February, 2015

Michelle K. Lee

Michelle K. Lee
*Deputy Director of the United States Patent and Trademark Office*

Lines 61-62, "D135317, D165539, D2S1338, D195433, vWA, TPDX, D18551," should read --D13S317, D16S539, D2S1338, D19S433, vWA, TP0X, D18S51,--.

Column 19,

Line 19, "Log 2ratio>0.15" should read --Log2ratio >0.15--.

SEQUENCE LISTING

<160> NUMBER OF SEQ ID NOS: 2

<210> SEQ ID NO 1
<211> LENGTH: 29
<212> TYPE: DNA
<213> ORGANISM: ARTIFICIAL SEQUENCE
<220> FEATURE:
<223> OTHER INFORMATION: PRIMER

<400> SEQUENCE: 1
atttgatgct gtccccggac gatattgaa 29

<210> SEQ ID NO 2
<211> LENGTH: 30
<212> TYPE: DNA
<213> ORGANISM: ARTIFICIAL SEQUENCE
<220> FEATURE:
<223> OTHER INFORMATION: PRIMER

<400> SEQUENCE: 2
cactccagcc acctgaagtc caaaaagggt 30